(12) United States Patent
Gilson et al.

(10) Patent No.: US 11,672,641 B2
(45) Date of Patent: Jun. 13, 2023

(54) VASCULAR FILTER SYSTEM

(71) Applicant: Novate Medical Limited, Dublin (IE)

(72) Inventors: Paul Gilson, Galway (IE); Steven Horan, Galway (IE); Karl Keating, Galway (IE); Aidan Goggin, Redcastle (IE)

(73) Assignee: Novate Medical Limited, Galway (IE)

( * ) Notice: Subject to any disclaimer, the term of this patent is extended or adjusted under 35 U.S.C. 154(b) by 338 days.

(21) Appl. No.: 16/807,613

(22) Filed: Mar. 3, 2020

(65) Prior Publication Data

US 2020/0197150 A1 Jun. 25, 2020

Related U.S. Application Data

(63) Continuation of application No. 15/379,115, filed on Dec. 14, 2016, now Pat. No. 10,624,731, which is a (Continued)

(51) Int. Cl.
*A61F 2/01* (2006.01)

(52) U.S. Cl.
CPC ............. *A61F 2/0103* (2020.05); *A61F 2/011* (2020.05); *A61F 2002/016* (2013.01); *A61F 2210/0004* (2013.01); *A61F 2230/005* (2013.01); *A61F 2230/0067* (2013.01); *A61F 2230/0069* (2013.01); *A61F 2230/0091* (2013.01);
(Continued)

(58) Field of Classification Search
None
See application file for complete search history.

(56) References Cited

U.S. PATENT DOCUMENTS

| 5,344,427 A | 9/1994 | Cottenceau et al. |
| 5,375,612 A | 12/1994 | Cottenceau et al. |

(Continued)

FOREIGN PATENT DOCUMENTS

| DE | 4030998 A1 | 4/1991 |
| DE | 102008031299 A1 | 1/2010 |

(Continued)

*Primary Examiner* — Sarah A Simpson
*Assistant Examiner* — Lindsey Bachman
(74) *Attorney, Agent, or Firm* — Seager, Tufte & Wickhem LLP

(57) ABSTRACT

A vascular filter system comprises a vascular filter (1), a clamp device (50), and a delivery catheter (51). The filter (1) comprises filter elements (6). When used without the clamp device (50), the filter elements (6) move from a closed state to an open state upon elapse of a predetermined period of time. In the closed state the filter elements (6) capture thrombus passing through the inferior vena cava (2). The delivery catheter (51) is employed to deliver the clamp device (50) to the filter (1) after the filter (1) has been deployed in the inferior vena cava (2). The clamp device (50) engages with the filter elements (6) of the filter (1) to clamp the filter (1) in the closed state beyond elapse of the predetermined period of time. Because of the presence of the clamp device (50), the filter elements (6) are no longer free to move from the closed state to the open state upon elapse of the predetermined period of time. In this manner the period of time in which the filter (1) captures thrombus is extended either temporarily or permanently.

12 Claims, 30 Drawing Sheets

Related U.S. Application Data continuation of application No. 12/688,173, filed on Jan. 15, 2010, now abandoned.

(60) Provisional application No. 61/145,387, filed on Jan. 16, 2009.

(52) U.S. Cl.
CPC . *A61F 2250/003* (2013.01); *A61F 2250/0031* (2013.01); *A61F 2250/0059* (2013.01)

(56) References Cited

U.S. PATENT DOCUMENTS

| | | | |
|---|---|---|---|
| 5,383,887 A | 1/1995 | Nadal | |
| 5,474,572 A | 12/1995 | Hayhurst | |
| 5,634,942 A | 6/1997 | Chevillon et al. | |
| 5,725,550 A | 3/1998 | Nadal | |
| 5,776,186 A | 7/1998 | Uflacker | |
| 5,800,525 A | 9/1998 | Bachinski et al. | |
| 5,853,420 A * | 12/1998 | Chevillon | A61F 2/0105 606/200 |
| 5,928,261 A | 7/1999 | Ruiz | |
| 5,968,071 A | 10/1999 | Chevillon et al. | |
| 6,193,739 B1 | 2/2001 | Chevillon et al. | |
| 6,203,550 B1 * | 3/2001 | Olson | A61F 2/954 606/108 |
| 6,214,025 B1 | 4/2001 | Thistle et al. | |
| 6,241,746 B1 | 6/2001 | Bosma et al. | |
| 6,248,128 B1 | 6/2001 | Berry et al. | |
| 6,267,776 B1 | 7/2001 | O'Connell | |
| 6,312,461 B1 | 11/2001 | Unsworth et al. | |
| 6,383,206 B1 | 5/2002 | Gillick et al. | |
| 6,482,227 B1 | 11/2002 | Solovay | |
| 6,517,559 B1 | 2/2003 | O'Connell | |
| 6,527,962 B1 | 3/2003 | Nadal | |
| 6,582,447 B1 | 6/2003 | Patel et al. | |
| 6,605,111 B2 | 8/2003 | Bose et al. | |
| 6,652,558 B2 | 11/2003 | Patel et al. | |
| 6,666,882 B1 | 12/2003 | Bose et al. | |
| 6,669,721 B1 | 12/2003 | Bose et al. | |
| 6,712,834 B2 | 3/2004 | Yassour et al. | |
| 6,852,076 B2 | 2/2005 | Nikolic et al. | |
| 6,881,218 B2 | 4/2005 | Beyer et al. | |
| 6,932,832 B2 | 8/2005 | Patel et al. | |
| 6,966,923 B2 | 11/2005 | Gittings | |
| 6,972,025 B2 | 12/2005 | WasDyke | |
| 7,001,424 B2 | 2/2006 | Patel et al. | |
| 7,094,248 B2 | 8/2006 | Bachinski et al. | |
| 7,261,731 B2 | 8/2007 | Patel et al. | |
| 7,279,007 B2 | 10/2007 | Nikolic et al. | |
| 7,534,251 B2 | 5/2009 | WasDyke | |
| 8,025,675 B2 | 9/2011 | Shirley et al. | |
| 2001/0044652 A1 | 11/2001 | Moore | |
| 2003/0120303 A1 | 6/2003 | Boyle et al. | |
| 2003/0176888 A1 | 9/2003 | O'Connell | |
| 2003/0208227 A1 | 11/2003 | Thomas | |
| 2004/0019374 A1 | 1/2004 | Hojeibane et al. | |
| 2004/0138677 A1 | 7/2004 | Little et al. | |
| 2004/0220611 A1 | 11/2004 | Ogle | |
| 2005/0096735 A1 | 5/2005 | Hojeibane et al. | |
| 2005/0107822 A1 | 5/2005 | WasDyke | |
| 2005/0121576 A1 | 6/2005 | Moran | |
| 2005/0222604 A1 | 10/2005 | Schaeffer | |
| 2005/0234504 A1 | 10/2005 | WasDyke | |
| 2005/0251197 A1 * | 11/2005 | Hensley | 606/200 |
| 2006/0025852 A1 | 2/2006 | Armstrong et al. | |
| 2007/0032816 A1 * | 2/2007 | O'Connell | A61F 2/0105 606/200 |
| 2007/0112372 A1 | 5/2007 | Sosnowski et al. | |
| 2007/0203571 A1 | 8/2007 | Kaplan et al. | |
| 2007/0227544 A1 * | 10/2007 | Swann | A61B 17/12163 128/831 |
| 2008/0027481 A1 | 1/2008 | Gilson et al. | |
| 2008/0188887 A1 | 8/2008 | Batiste | |
| 2008/0208245 A1 | 8/2008 | Hoffman | |
| 2009/0157115 A1 | 6/2009 | Fleming | |
| 2009/0163926 A1 | 6/2009 | Sos | |
| 2009/0299404 A1 | 12/2009 | Chanduszko et al. | |
| 2010/0042135 A1 * | 2/2010 | Shirley | A61F 2/01 128/898 |
| 2010/0185227 A1 | 7/2010 | Horan et al. | |
| 2010/0185229 A1 | 7/2010 | Horan et al. | |
| 2010/0185230 A1 | 7/2010 | Horan et al. | |

FOREIGN PATENT DOCUMENTS

| | | |
|---|---|---|
| EP | 0555395 A1 | 8/1993 |
| EP | 0582493 A1 | 2/1994 |
| EP | 0598635 A1 | 5/1994 |
| EP | 0605276 A1 | 7/1994 |
| EP | 0655228 A1 | 5/1995 |
| EP | 0678284 A1 | 10/1995 |
| EP | 0737451 A1 | 10/1996 |
| EP | 0759287 A1 | 2/1997 |
| EP | 0935975 A1 | 8/1999 |
| EP | 1103233 A1 | 5/2001 |
| EP | 1258228 A1 | 11/2002 |
| EP | 1616530 A1 | 1/2006 |
| FR | 2718950 A1 | 10/1995 |
| FR | 2764503 A1 | 12/1998 |
| FR | 2814670 A1 | 4/2002 |
| WO | 0056390 A1 | 9/2000 |
| WO | 0066031 A1 | 11/2000 |
| WO | 0162184 A2 | 8/2001 |
| WO | 0222048 A2 | 3/2002 |
| WO | 2006020425 A1 | 2/2006 |
| WO | 2006074163 A2 | 7/2006 |
| WO | 2006107939 A1 | 10/2006 |
| WO | 2006116636 A1 | 11/2006 |
| WO | 2007064731 A2 | 6/2007 |
| WO | WO 2007/064731 * | 6/2007 |
| WO | WO 2007/064731 A2 * | 6/2007 |
| WO | 2007079407 A2 | 7/2007 |
| WO | 2008010197 A2 | 1/2008 |
| WO | 2010025775 A1 | 3/2010 |

* cited by examiner

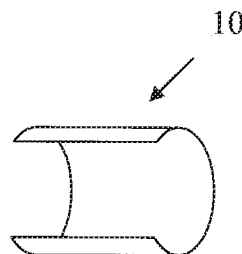
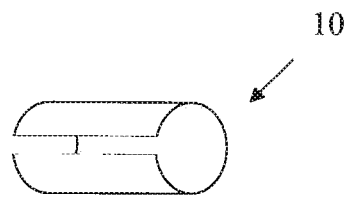
Fig. 9  Fig. 10
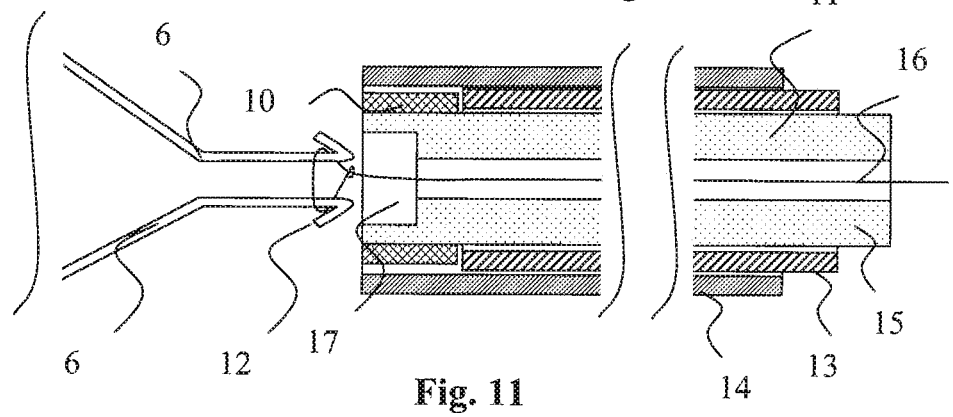
Fig. 11
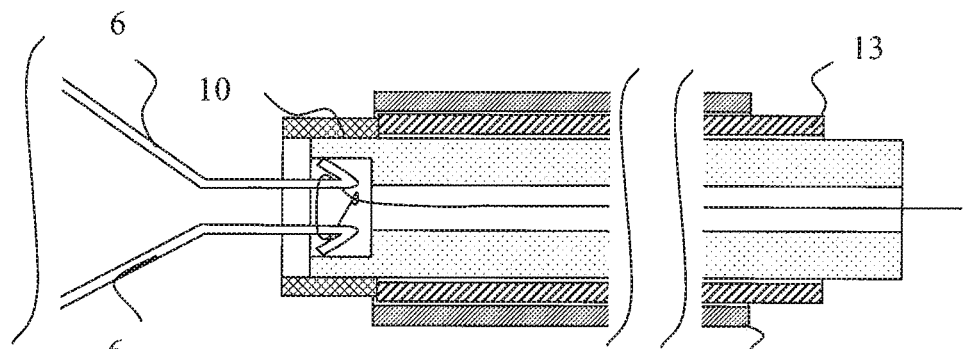
Fig. 12
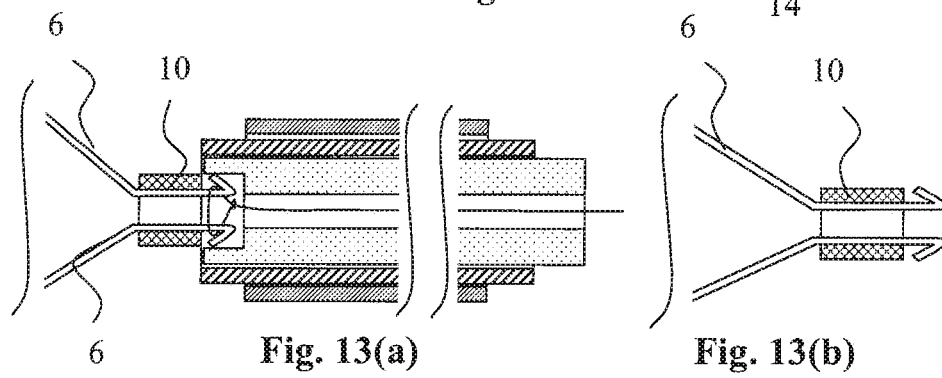
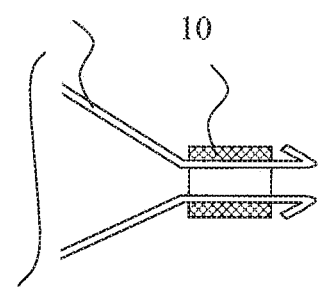
Fig. 13(a)  Fig. 13(b)

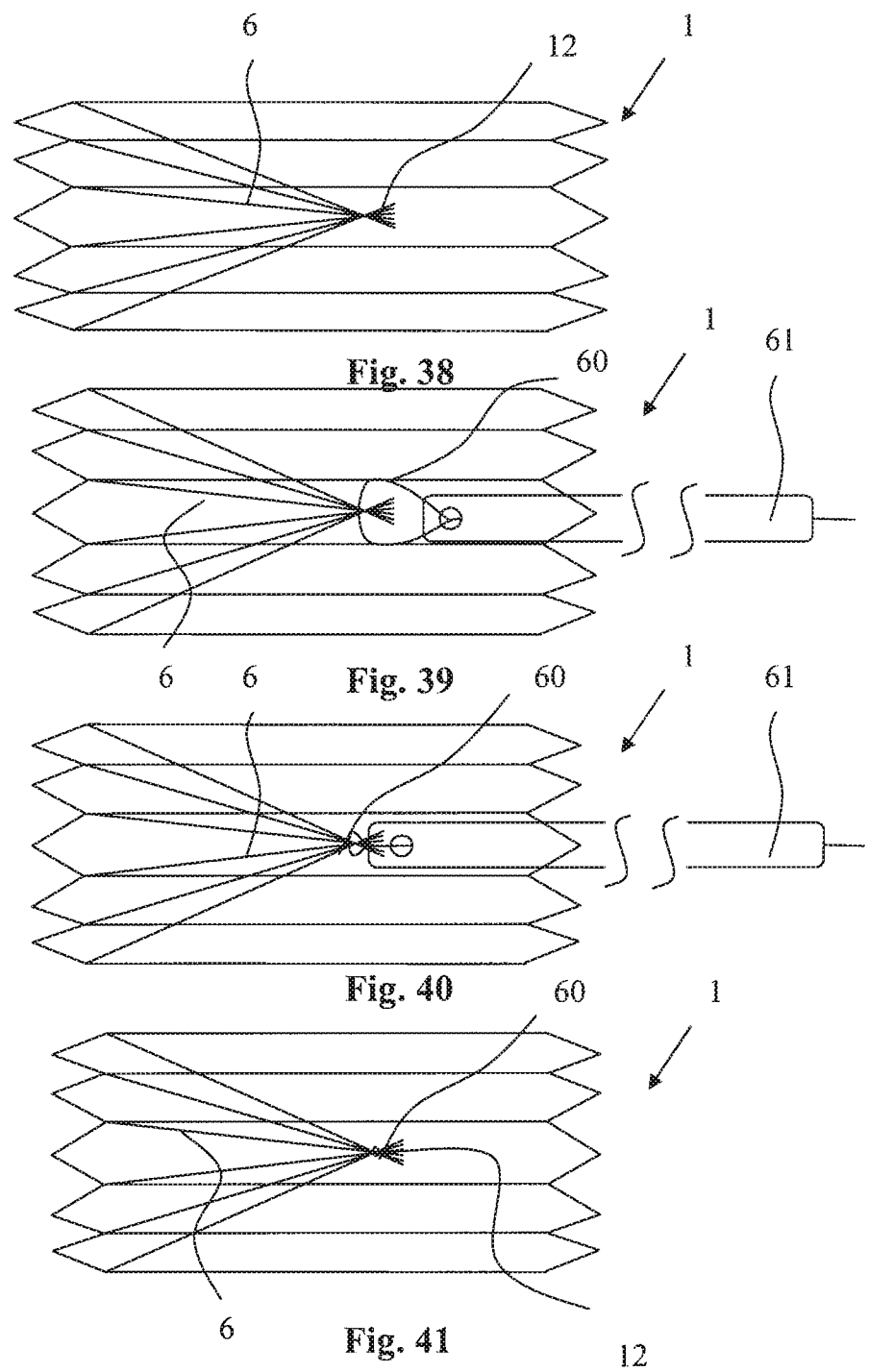

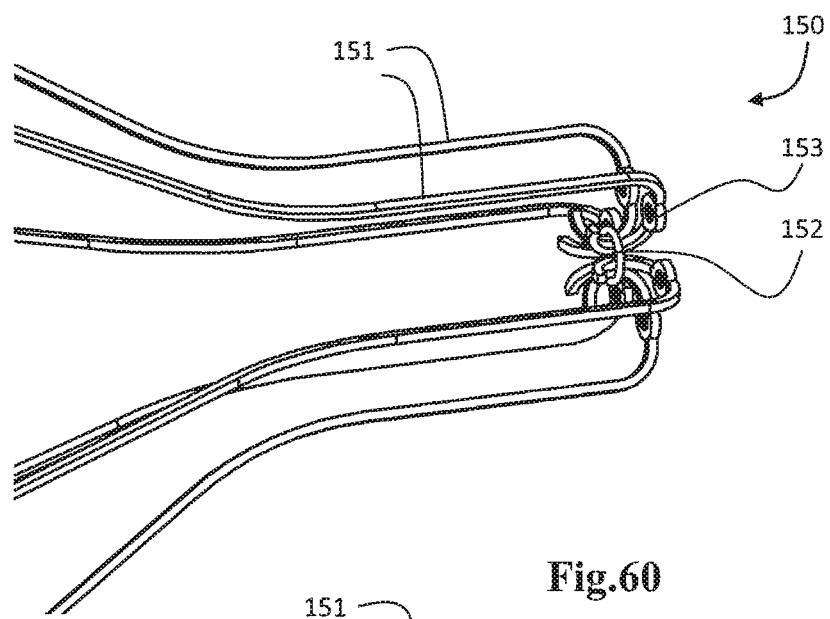
Fig.60
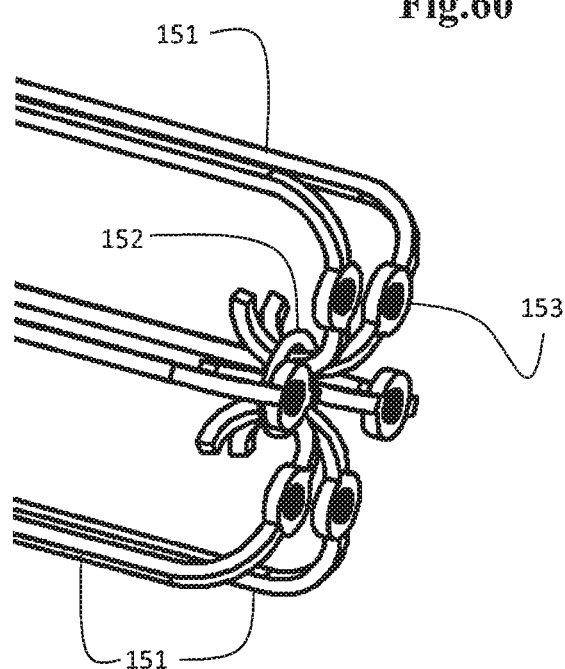
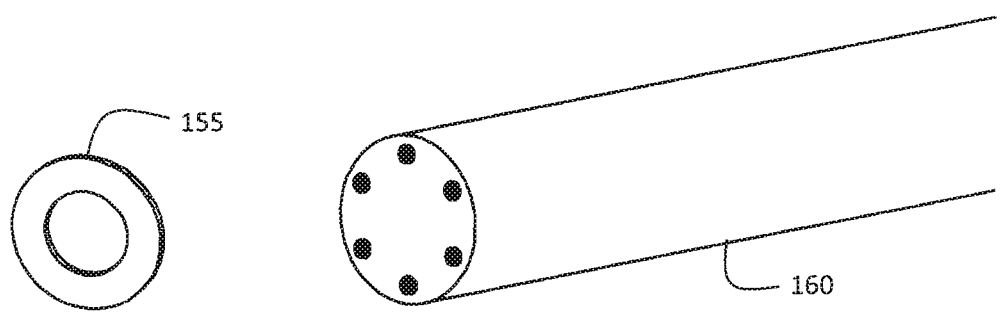
Fig.61

VASCULAR FILTER SYSTEM

RELATED APPLICATIONS

This application is a continuation of U.S. patent application Ser. No. 15/379,115 filed Dec. 14, 2016, which is a continuation of U.S. patent application Ser. No. 12/688,173 filed Jan. 15, 2010, which claims the benefit of priority from U.S. Provisional Application No. 61/145,387 filed on Jan. 16, 2009, the entire contents of which are incorporated herein by reference.

INTRODUCTION

This invention relates to a vascular filter system.

WO2008/010197 describes a vascular filter having filter elements which are held by a holder in a closed state for capturing thrombus passing through a blood vessel. The filter opens when the holder biodegrades after a predetermined period of time.

The invention is directed towards providing more versatility in use of a filter after delivery.

SUMMARY OF THE INVENTION

According to the invention, there is provided a vascular filter system comprising a vascular filter comprising at least one filter element, the filter being movable from a closed state for capturing thrombus passing through a blood vessel to an open state facilitating unrestricted blood flow. There may be a holder for holding the filter in the closed state for a predetermined period of time. There may be a member to at least temporarily extend the filtration period.

In one embodiment, the member comprises a retainer to at least temporarily retain the filter in the closed state beyond elapse of the predetermined period of time.

In one embodiment, the retainer is extendable around at least part of the filter to retain the filter in the closed state. In one embodiment, the retainer is adapted to clamp at least part of the filter to retain it in the closed state. In one embodiment, the retainer is adapted to tie at least part of the filter to retain it in the capturing state. In one embodiment, the retainer is configured to be located in the region of the centre of the filter. In one embodiment, the retainer is configured to be located in the region of the side of the filter. In one embodiment, at least part of the retainer is biodegradable and/or bioabsorbable. In one embodiment, the retainer is biostable. In one embodiment, the retainer is movable between a delivery state and a retaining state.

In one embodiment, the retainer is biased towards the retaining state. In one embodiment, the system comprises a delivery mechanism to deliver the retainer to the filter located in the blood vessel. In one embodiment, the delivery mechanism is adapted to maintain the position of the filter relative to a blood vessel during delivery of the retainer. In one embodiment, the delivery mechanism is adapted to grasp the filter for delivery of the retainer. In one embodiment, the retainer is configured to releasably retain the filter in the closed state. In one embodiment, the retainer is changeable, when engaging the filter, from a non-retaining state in which the filter is not retained to a retaining state in which the filter is retained. In one embodiment, the retainer is changeable from the non-retaining state to the retaining state responsive to an external intervention. In one embodiment, the retainer is changeable by rotation on threads to move with respect to the filter. In one embodiment, the retainer is changeable by insertion of a magnetic part to retain the filter.

In one embodiment, the retainer comprises first magnetic parts on the filter elements and a second magnetic part for engagement with the first magnetic parts to retain the filter elements in the closed state. In one embodiment, the first magnetic parts are located on the filter elements so that they are in a plane when the filter is in the closed state, and the second magnetic part has a planar face for contacting the first magnetic parts. In one embodiment, the second magnetic part is annular or disc-shaped.

In one embodiment, the system comprises a delivery assembly including a delivery catheter having a magnetic attraction to the second magnetic part which is less than the magnetic attraction between the first magnetic parts and the second magnetic part.

In one embodiment, the second magnetic part is sleeve-shaped, and the first magnetic parts are arranged in a ring which fits within the sleeve when the filter is in the closed state.

In one embodiment, the retainer is cup-shaped and configured to snap-fit around the ends of the filter elements. In one embodiment, the filter elements have arrow-shaped tips to fit behind a rim of the retainer. In one embodiment, the filter is biased towards the open state.

In one embodiment, at least part of the retainer is extendable through an opening between adjacent filter elements to retain the filter elements in the closed state beyond elapse of the predetermined period of time.

In one embodiment, at least part of the retainer is extendable through an opening in a filter element to retain the filter elements in the closed state beyond elapse of the predetermined period of time.

In one embodiment, in the closed state the filter elements extend towards an apex. In one embodiment, the retainer is configured to be located in the region of the apex. In one embodiment, the retainer is configured to be located in the region of the end of the filter element opposite to the apex.

In one embodiment, at least part of the holder is biodegradable and/or bioabsorbable upon elapse of the predetermined period of time.

In one embodiment, the filter comprises a vena cava filter.

In another aspect, the invention provides a method for treating a blood vessel, the method comprising the steps of:—[0019] locating a vascular filter in the blood vessel, the vascular filter comprising at least one filter element, the filter being movable after a predetermined period of time from a closed state for capturing thrombus passing through the blood vessel to an open state facilitating unrestricted blood flow, and [0020] a retainer at least temporarily retaining the filter in the capturing state beyond elapse of the first predetermined period of time.

In one embodiment, the method comprises the step of delivering the retainer to the filter. In one embodiment, the retainer is delivered to the filter after the filter has been located in the blood vessel. In one embodiment, the retainer is delivered to the filter using a delivery mechanism, and the method comprises the step of centering the delivery mechanism in the blood vessel. In one embodiment, the method comprises the step of maintaining the position of the filter relative to the blood vessel during delivery of the retainer.

In one embodiment, the method comprises the step of grasping the filter before delivering the retainer. In one embodiment, the method comprises the step of changing the retainer while it engages the filter from a non-retaining state in which the filter is not retained to a retaining state in which the filter is retained.

In one embodiment, the retainer is changed from the non-retaining state to the retaining state by external intervention. In one embodiment, the retainer is moved with respect to the filter.

In one embodiment, the retainer is rotated to move on threads. In one embodiment, the retainer is pushed or pulled with respect to the filter.

In one embodiment, the intervention includes inserting a retainer magnetic part for retaining the filter elements in the closed state. In one embodiment, the method comprises the step of extending the retainer around at least part of the filter. In one embodiment, at least part of the retainer biodegrades and/or is bioabsorbed upon elapse of a second predetermined period of time. In one embodiment, the method comprises the step of removing the retainer from the filter.

A vascular system configured to replace bioresorbable materials in vascular devices with a biostable component.

BRIEF DESCRIPTION OF THE DRAWINGS

The invention will be more clearly understood from the following description of some embodiments thereof, given by way of example only, with reference to the accompanying drawings, in which:

FIG. 9 is an isometric view of a retaining means part of the vascular filter system according to the invention in a delivery configuration, FIG. 10 is an isometric view of the retaining means part of FIG. 9 in a retaining configuration, FIGS. 11 to 18 are cross sectional side views of the vascular filter part of FIG. 1 and the retaining means part of FIG. 9 in use, FIGS. 38 to 41 are views similar to FIGS. 11 to 13(b) of another vascular filter system according to the invention in use, FIG. 60 is a perspective view of a filter with magnetic retainer elements, and FIG. 61 shows the filter in more detail together with a second magnetic part delivered by a catheter.

DETAILED DESCRIPTION

Figure 1:
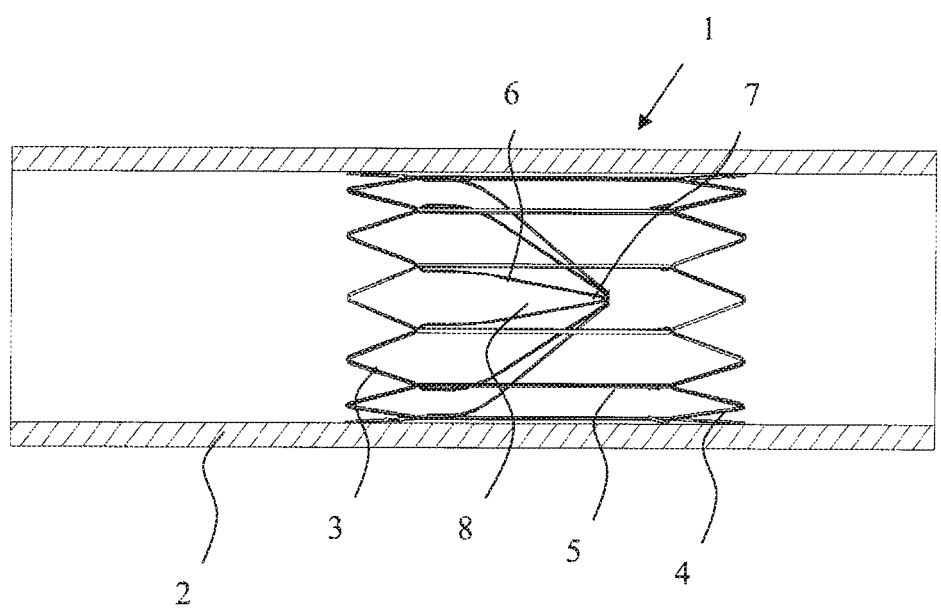
FIG. 1 is a side view of a vascular filter part of a vascular filter system according to the invention located in a blood vessel.

Referring to the drawings, and initially to FIGS. 1 to 18 thereof, there is illustrated a vascular filter system according to the invention. The vascular filter system comprises a vascular filter 1, a retainer 10, and a delivery catheter 11.

Figure 4:
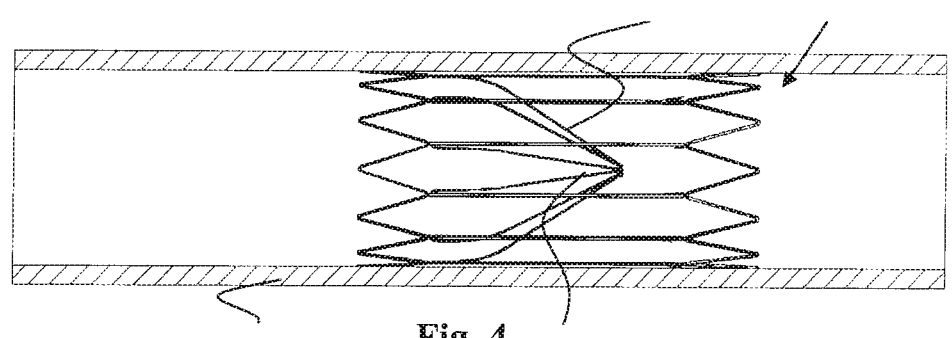
Figure 5:
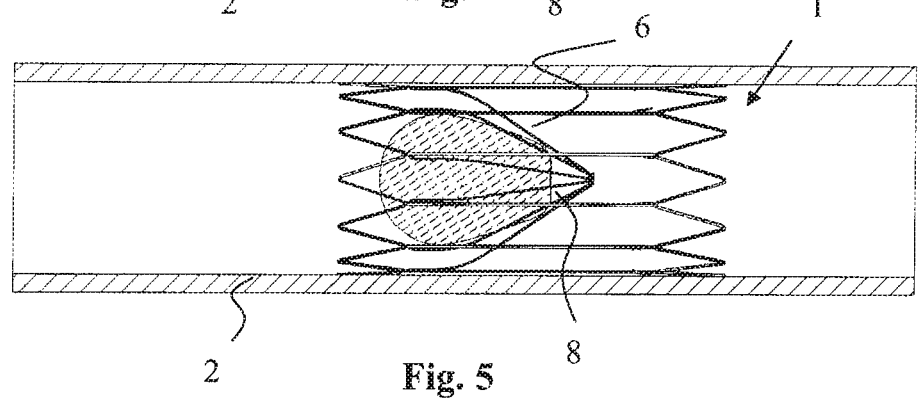

The vascular filter 1 is suitable for use as an inferior vena cava filter in the inferior vena cava 2. When used without the retainer 10, the filter 1 is movable from a closed state (FIG. 4) to an open state (FIG. 7) upon elapse of a predetermined period of time. In the closed state the filter 1 captures thrombus passing through the inferior vena cava 2 towards the heart and the lungs (FIG. 5). The filter 1 may thus be used to prevent pulmonary embolism. In the open state the filter 1 facilitates unrestricted blood flow.

As illustrated in FIG. 1, the filter 1 comprises a proximal support hoop 3 at the proximal end of the filter 1, a distal support hoop 4 at the distal end of the filter 1, and a plurality of support struts 5 extending between the proximal support hoop 3 and the distal support hoop 4.

In this patent specification, the terms 'proximal' and "distal" are used in the sense that a proximal part is upstream of a distal part with reference to the direction of blood flow.

The proximal support hoop 3 comprises a wire element which extends circumferentially around the internal wall of the inferior vena cava 2 in a sinusoid wave pattern. Similarly the distal support hoop 4 comprises a wire element which extends circumferentially around the internal wall of the inferior vena cava 2 in a sinusoid wave pattern. The support struts 5 extend longitudinally along the internal wall of the inferior vena cava 2. The support struts 5 connect the proximal support hoop 3 to the distal support hoop 4. In this case the proximal support hoop 3, the distal support hoop 4 and the support struts 5 are formed integrally. The proximal support hoop 3, the distal support hoop 4 and the support struts 5 may be of a shape-memory material, such as Nitinol™.

As illustrated in FIG. 1, the filter 1 comprises twelve filter elements 6 for capturing thrombus passing through the inferior vena cava 2. Each filter element 6 is formed integrally with the proximal support hoop 3.

In the closed state the filter elements 6 extend in a substantially straight line to an apex 7, where the filter elements 6 engage each other. In this manner the filter elements 6 define a generally conically shaped capture region 8 within which thrombus may be captured. When the filter 1 is deployed in the inferior vena cava 2, the apex 7 is substantially in-line with the longitudinal axis extending through the centre of the inferior vena cava 2, and the capture region 8 is located in the region of the centre of the inferior vena cava 2. When the filter 1 is deployed in the inferior vena cava 2, the filter elements 6 extend in the direction of blood flow through the inferior vena cava 2.

The distal end of the distal support hoop 4 is located distally of the filter elements 6 and the apex 7, and the proximal end of the proximal support hoop 3 is located proximally of the filter elements 6.

When used without the retainer 10, the filter elements 6 are movable from the closed state to the open state upon elapse of the predetermined period of time. The filter elements 6 are biased towards the open state, and a holder is provided at the distal ends of the filter elements 6 to temporarily hold the filter elements 6 in the closed state until elapse of the predetermined period of time. The holder is biodegradable and/or bioabsorbable upon elapse of the predetermined period of time. When used without the retainer 10, upon biodegrading/bioabsorbing of the holder, the filter elements 6 are free to move from the closed state to the open state. The filter elements 6 are not biodegradable or bioabsorbable.

The holder may be provided in the form of a holder tube, or alternatively in the form of a holder suture extended through an opening at the distal end of each of the filter elements 6.

The filter 1 is movable between a collapsed delivery state and an expanded deployed state. The filter 1 is biased radially outwardly towards the deployed state. When the filter 1 is deployed in the inferior vena cava 2, the support hoops 3, 4 exert a force radially outwardly on the internal wall of the inferior vena cava 2. In this manner the support hoops 3, 4 support the filter elements 6 in position relative to the wall of the inferior vena cava 2.

The retainer 10 acts to at least temporarily retain the filter 1 in the closed state beyond elapse of the predetermined period of time.

In this case the retainer 10 is provided in the form of a clamp tube. The clamp tube is movable between a delivery state (FIG. 9) and a retaining state (FIG. 10). The clamp tube 10 is biased towards the retaining state.

In the retaining state the clamp tube 10 extends around the distal ends of the filter elements 6 of the filter 1 to retain the filter 1 in the closed state (FIG. 13(*b*)) beyond elapse of the predetermined period of time. In particular, in the retaining state the clamp tube 10 engages with the filter elements 6 of the filter 1 to clamp the filter 1 in the closed state. In the retaining state the clamp tube 10 is located in the region of the apex 7 of the filter 1 at the centre of the filter 1.

Because of the presence of the clamp tube 10, the filter elements 6 are no longer free to move from the closed state to the open state upon elapse of the predetermined period of time. Upon biodegrading/bioabsorbing of the holder, the filter elements 6 of the filter 1 are retained in the closed state by the clamp tube 10. In this manner the period of time in which the filter 1 captures thrombus is extended either temporarily or permanently.

The clamp tube 10 may be biodegradable and/or bioabsorbable. This results in a temporary extension of the period of time in which the filter 1 may capture thrombus. Alternatively the clamp tube 10 may be biostable. This results in a permanent extension of the period of time in which the filter 1 may capture thrombus. The temporary filter 1 may be converted into a permanent filter, or the life of the filter 1 may be prolonged.

An inclined lip 12 is provided at the distal end of each filter element 6. The lips 12 are engageable with the clamp tube 10 in the retaining configuration to releasably couple the clamp tube 10 in position around the distal ends of the filter elements 6 of the filter 1 (FIG. 13(*b*)).

As illustrated in FIGS. 14 to 18, the lips 12 may be invertable to facilitate selective removal of the clamp tube 10 from the distal ends of the filter elements 6 of the filter 1.

The delivery catheter 11 is employed to deliver the clamp tube 10 to the filter 1 after the filter 1 has been deployed in the inferior vena cava 2. The delivery catheter 11 comprises an inner tube 15 upon which the clamp tube 10 is mounted in the delivery configuration, an outer sheath 14, a pusher member 13 intermediate the inner tube 15 and the outer sheath 14, and a grasping wire 16 for grasping the distal ends of the filter elements 6 of the filter 1. The grasping wire 16 may be used to maintain the position of the filter 1 relative to the inferior vena cava 2 during delivery of the clamp tube 10. A recess 17 is provided at the proximal end of the inner tube 15 to facilitate positioning of the clamp tube 10 around the distal ends of the filter elements 6 of the filter 1 (FIG. 12).

Figure 2:
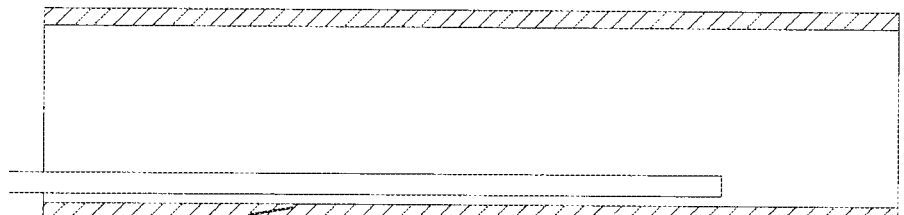
FIGS. 2 to 8 are side views of the vascular filter part of FIG. 1 in use in the blood vessel.
Figure 3:
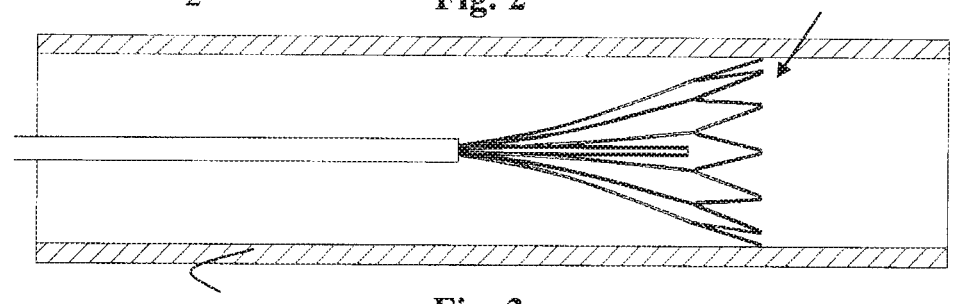

In use, the filter 1 is collapsed to the delivery state, and at least partially loaded into a delivery catheter. The delivery catheter is advanced through the inferior vena cava 2 until the collapsed filter 1 reaches the desired location in the inferior vena cava 2 (FIG. 2). A restraining sheath of the delivery catheter is then moved relative to the filter 1 to fully uncover the filter 1 (FIG. 3). Due to the biasing nature of the filter 1, the filter 1 moves from the collapsed delivery state to the expanded deployed state (FIG. 4). In the deployed state, the support hoops 3, 4 exert a radially outward force on the internal wall of the inferior vena cava 2 to support the filter elements 6 in the desired position in the inferior vena cava 2.

Figure 6:
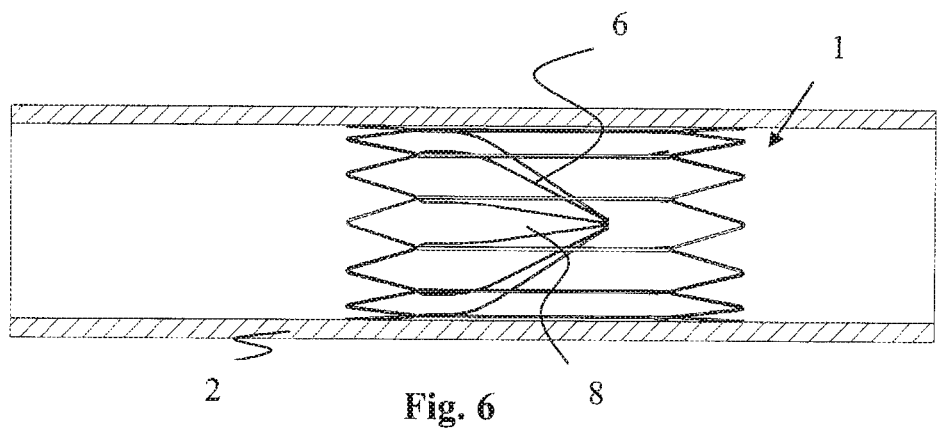

In the event of thrombus passing through the inferior vena cava 2 towards the heart and the lungs, the thrombus will be captured in the capture region 8 of the filter 1 (FIG. 5). The thrombus will thus be prevented from passing into the heart and the lungs which could otherwise lead to pulmonary embolism. The captured thrombus will gradually be broken down by the body into smaller size particles which will significantly reduce the risk of embolism (FIG. 6).

The holder temporarily holds the filter elements 6 in the closed state until elapse of the predetermined period of time. Before elapse of the predetermined period of time, the clamp tube 10 is mounted in the delivery state on the inner tube 15 of the delivery catheter 11. The delivery catheter 11 is advanced through the inferior vena cava 2 until the clamp tube 10 reaches the distal ends of the filter elements 6 of the filter 1, which has previously been deployed in the inferior vena cava 2 (FIG. 11). The grasping wire 16 is looped around the distal ends of the filter elements 6 of the filter 1 to hold the filter 1 relative to the delivery catheter 11 and to maintain the position of the filter 1 relative to the inferior vena cava 2 (FIG. 11). The outer sheath 14 is retracted to uncover the clamp tube 10 (FIG. 12). The delivery catheter 11 is advanced further through the inferior vena cava 2 until the lips 12 are within the recess 17 (FIG. 12). The pusher member 13 is moved proximally relative to the inner tube 15 until the clamp tube 10 is positioned around the distal ends of the filter elements 6 of the filter 1. Due to the biasing nature of the clamp tube 10, the clamp tube 10 moves from the delivery state to the retaining state (FIG. 13(*a*)).

In the retaining state the clamp tube 10 engages with the filter elements 6 of the filter 1 to clamp the filter 1 in the closed state beyond elapse of the predetermined period of time. Upon elapse of the predetermined period of time the holder biodegrades/bioabsorbs. The filter elements 6 of the filter 1 are retained in the closed state by the clamp tube 10. In this manner the period of time in which the filter 1 captures thrombus is extended either temporarily or permanently.

Figure 7:
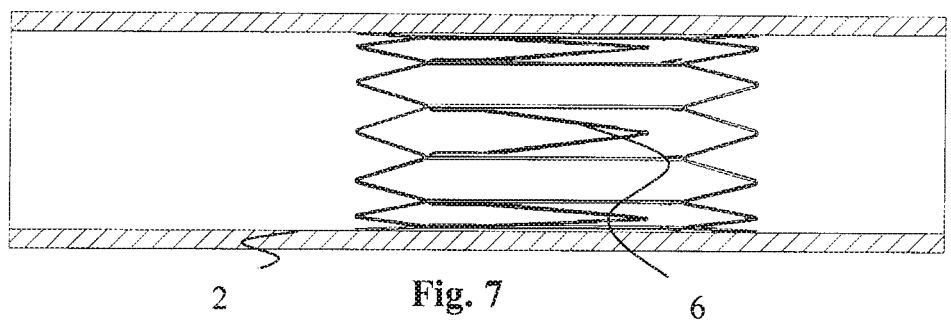
Figure 8:
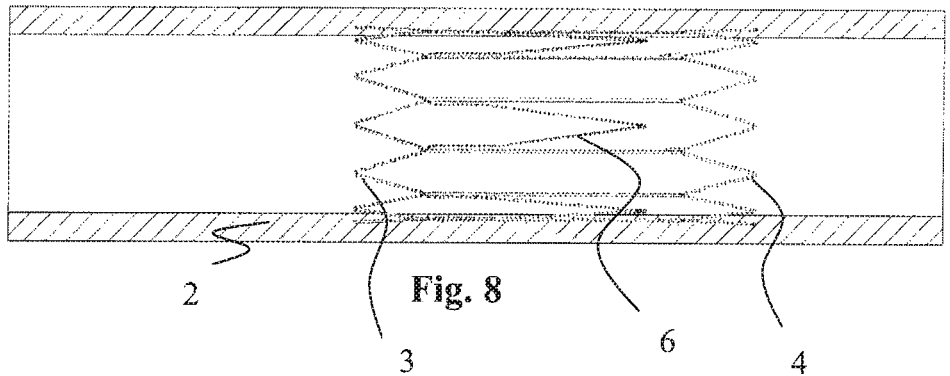
Figure 14:
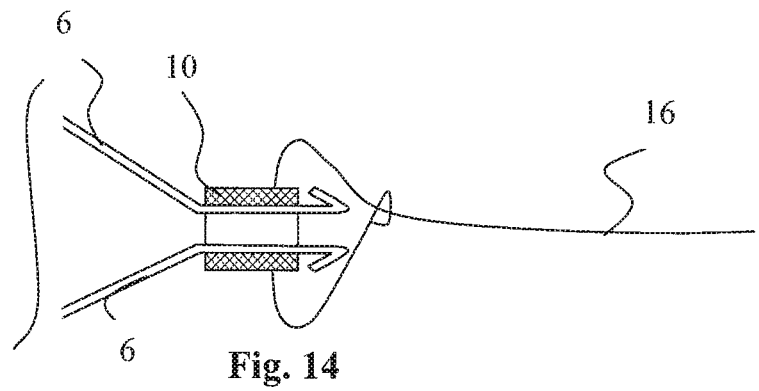

In the case where the clamp tube 10 is biodegradable and/or bioabsorbable, the clamp tube 10 biodegrades/bioabsorbs upon elapse of a further predetermined period of time. This enables the filter elements 6 to move from the closed state to the open state (FIG. 7). In the open state the filter 1 facilitates unrestricted blood flow. The support hoops 3, 4 and the filter elements 6 remain in the inferior vena cava 2 (FIG. 8).

In the case where the clamp tube 10 is biostable, the fitter 1 is permanently retained in the closed state (FIG. 6).

Figure 15:
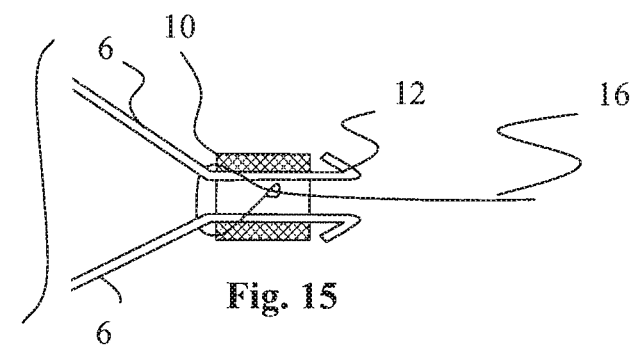
Figure 16:
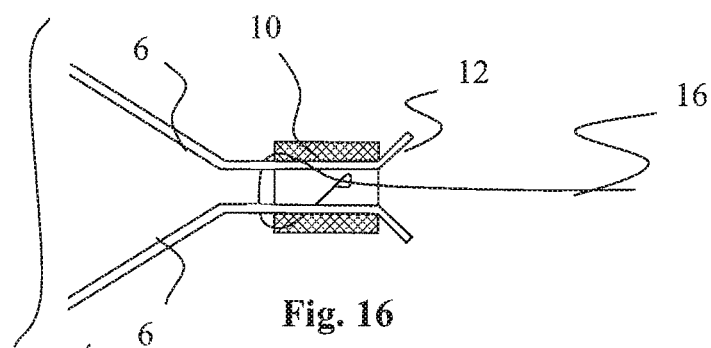
Figure 17:
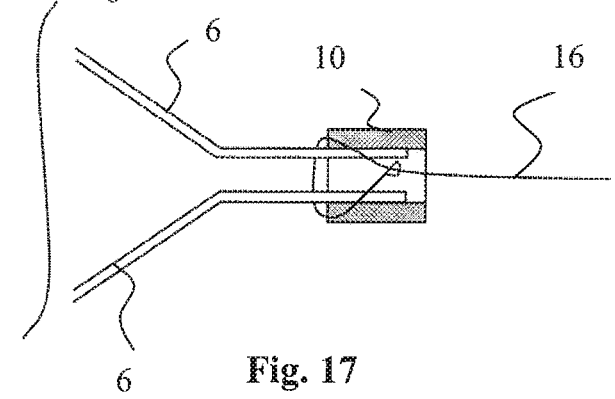

In the case of either the biodegradable/bioabsorbable clamp tube 10 or the biostable clamp tube 10, to remove the clamp tube 10 from the distal ends of the filter elements 6 of the filter 1, the grasping wire 16 is looped around the proximal end of the clamp tube 10 (FIG. 15). The grasping wire 16 is moved distally relative to the filter 1 to draw the clamp tube 10 distally causing inversion of the lips 12 (FIG. 16), and removal of the clamp tube 10 from the distal ends of the filter elements 6 of the filter 1 (FIG. 17). If the clamp tube 10 is removed after elapse of the predetermined period of time, the filter elements 6 move from the closed state to the open state (FIG. 7). In the open state the filter 1 facilitates unrestricted blood flow. The support hoops 3, 4 and the filter elements 6 remain in the inferior vena cava 2 (FIG. 8).

FIG. 11 illustrates the lasso/snare 16 threaded over the hooks 12 and tightened. Once the hooks 12 enter the hook dock 17 which occurs during tightening and prevents the biostable ring 10 from being deployed over the hooks 12, the snare 16, the centring shaft 15, and the outer sheath 14 are held stationary while the pusher 13 is advanced to deploy the biostable ring 10 between the implant filtration elements 6 and the hooks 12.

FIGS. 12 and 13(*a*) illustrate the biostable ring 10 moving from the undeployed expanded state to the deployed contracted state. The centring shaft 15 holds the biostable ring 10 in the expanded state during delivery. Once the pusher 13 advances the biostable ring 10 proximal of the centring shaft 15, the biostable ring 10 reverts to its natural contracted state. This phase transition may be achieved through the use of a spring or shape memory material It may be desirable to remove the biostable ring 10 once the patient has fully recovered (FIG. 17). This can be achieved through the use of the snare 16.

Figure 18:
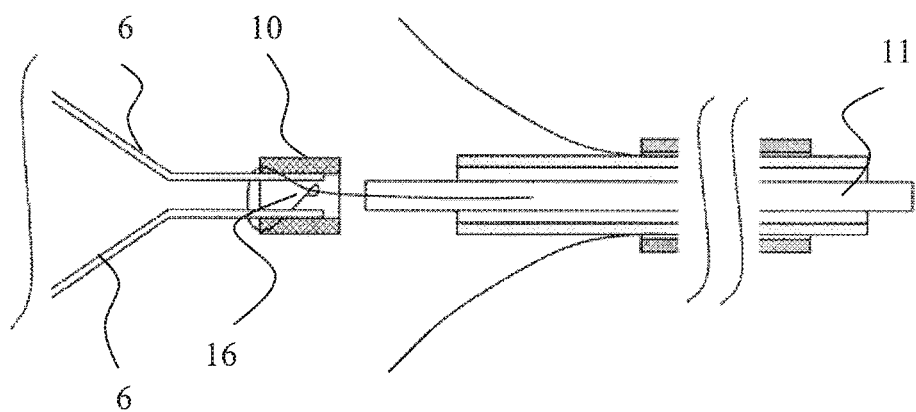

In order to prevent complications arising from the biostable ring 10 flowing loose in the venous system, a catch may be employed to aid retrieval of the biostable ring 10 (FIG. 18). The catch feature may be in the form of a retrieval catheter housed over the snare device 16 consisting of an expandable tip.

Figure 19:
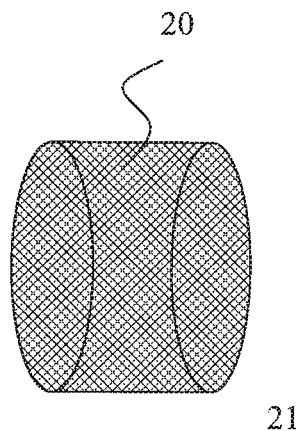
FIGS. 19 and 20 are views similar to FIGS. 9 and 10 of a retaining means part of another vascular filter system according to the invention.
Figure 20:
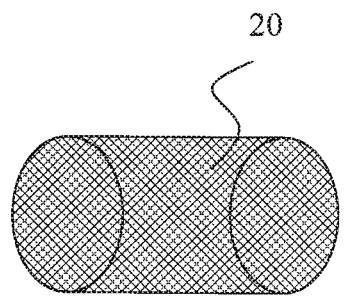
Figure 21:
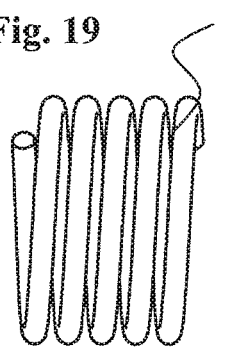
FIGS. 21 and 22 are views similar to FIGS. 9 and 10 of a retaining means part of another vascular filter system according to the invention.
Figure 22:
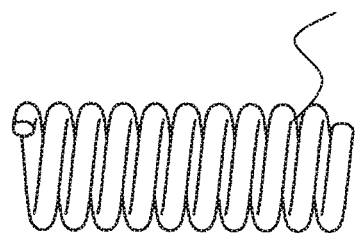
Figure 23:
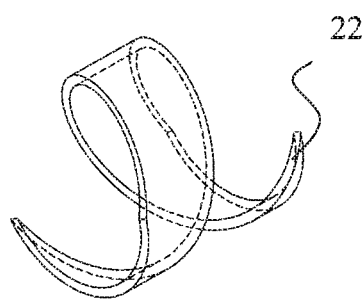
FIGS. 23 and 24 are views similar to FIGS. 9 and 10 of a retaining means part of another vascular filter system according to the invention.
Figure 24:
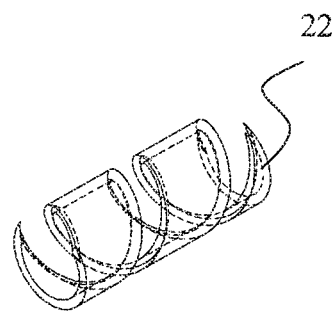

It will be appreciated that the retainer may be provided in any suitable form, for example a tubular mesh 20 (FIGS. 19 and 20), or a coil 21 (FIGS. 21 and 22), or a cut tube 22 (FIGS. 23 and 24).

Figure 25:
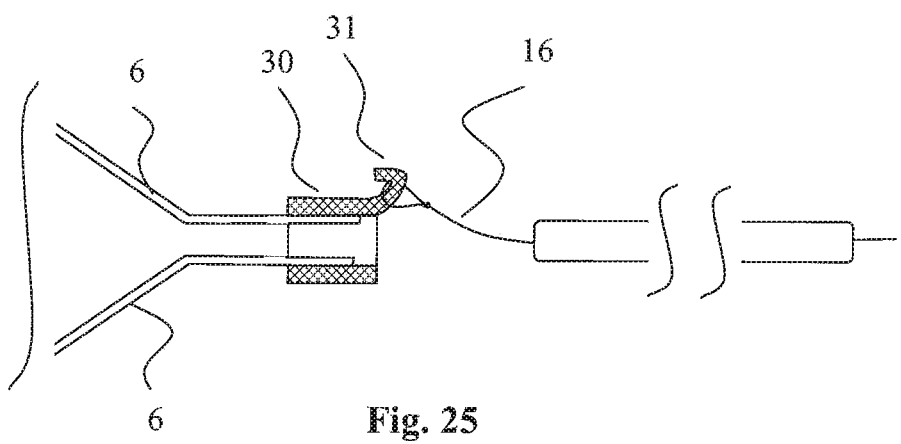
FIG. 25 is a view similar to FIG. 18 of another vascular filter system according to the invention in use.
Figure 26:
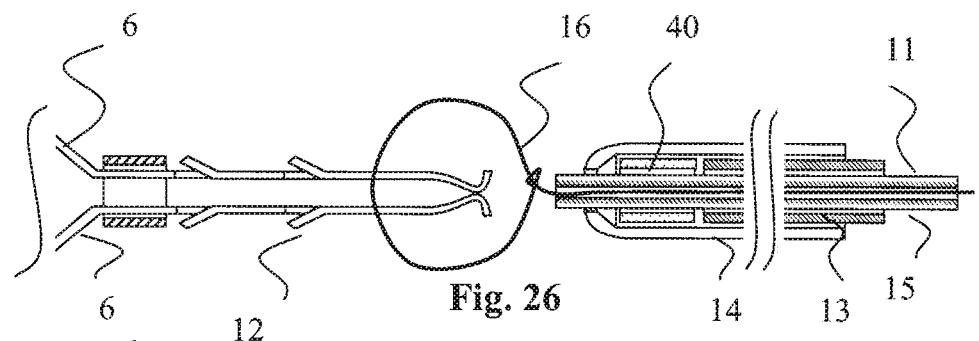
FIGS. 26 to 29 are views similar to FIGS. 11 to 13(b) of another vascular filter system according to the invention in use.

The retainer 30 may comprise an engagable protrusion 31 around which the grasping wire 16 may be looped to assist removal of the retainer 30 from the distal ends of the filter elements 6 of the filter 1 (FIG. 25). The catch feature may be in the form of the hook 31 connected/formed as part of the ring 30. This embodiment may also encompass a receiver mouth on the distal end of the snare catheter to facilitate removal of the biostable ring 30.

In FIGS. 26 to 29 there is illustrated another vascular filter system according to the invention, which is similar to the vascular filter system of FIGS. 1 to 18, and similar elements in FIGS. 26 to 29 are assigned the same reference numerals.

Figure 29:
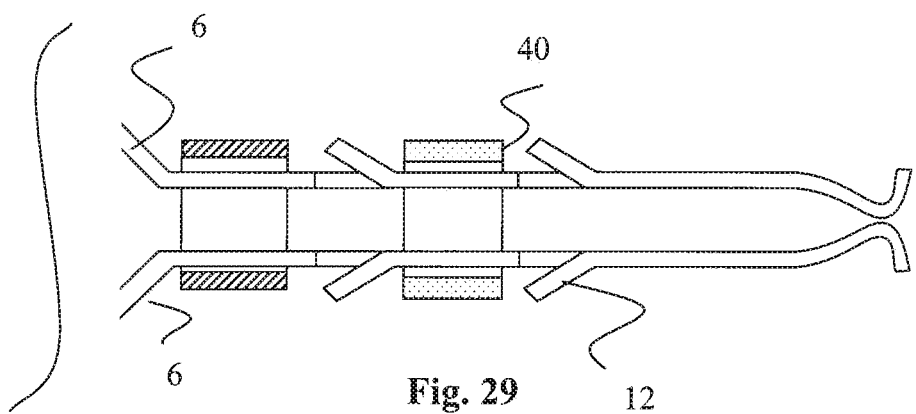
Figure 29A:
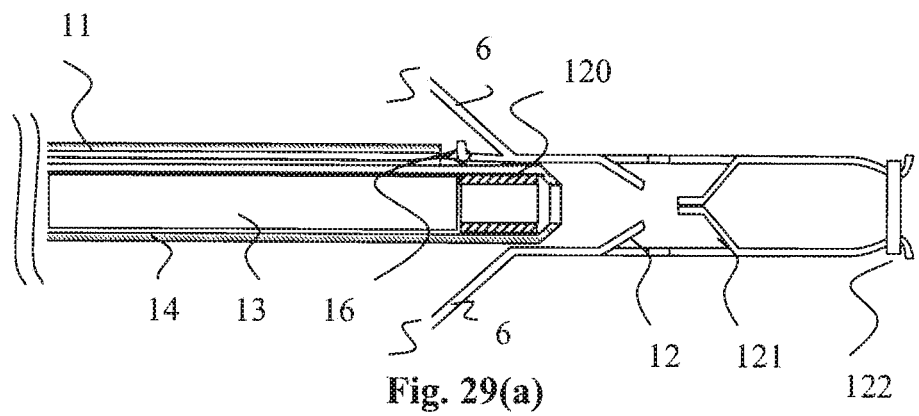
FIGS. 29(a) to 29(d) are views similar to FIGS. 11 to 13(b) of another vascular filter system according to the invention in use.
Figure 29B:
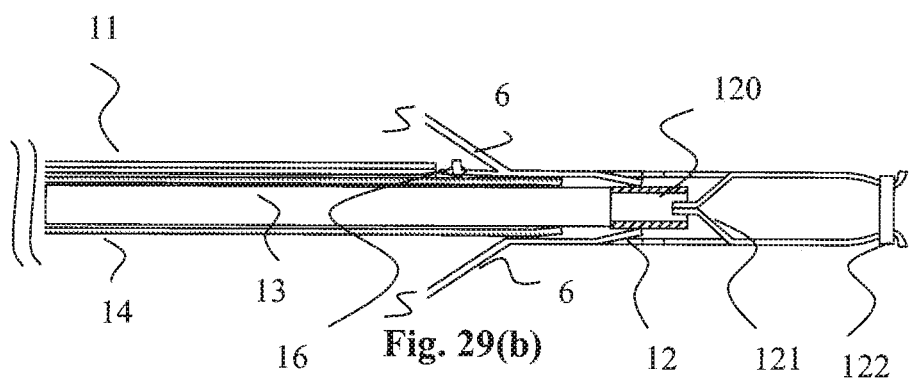
Figure 29C:
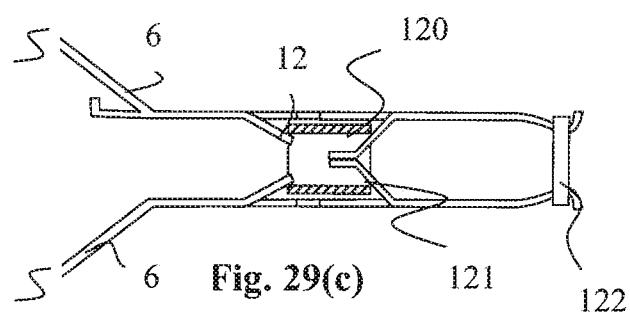
Figure 29D:
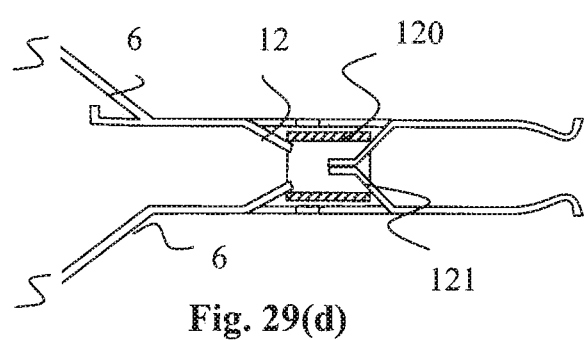
Figure 29E:
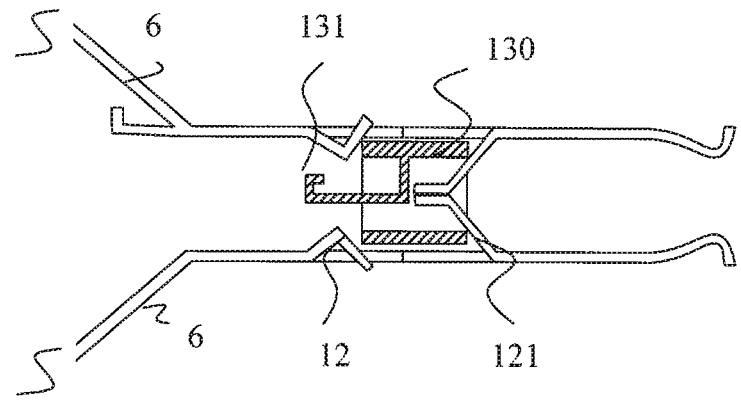
FIGS. 29(e) to 29(g) are views similar to FIGS. 14 to 18 of another vascular filter system according to the invention in use.
Figure 29F:
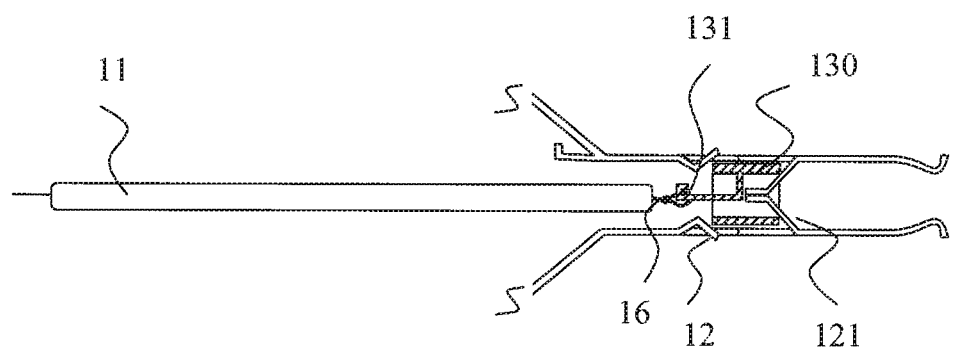
Figure 29G:
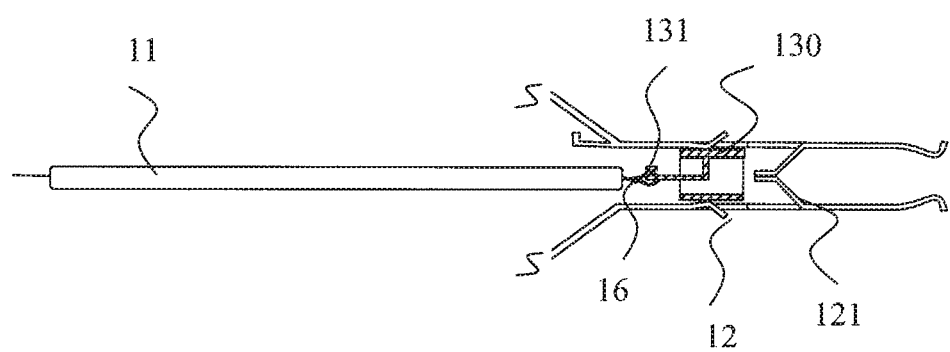
Figure 29H:
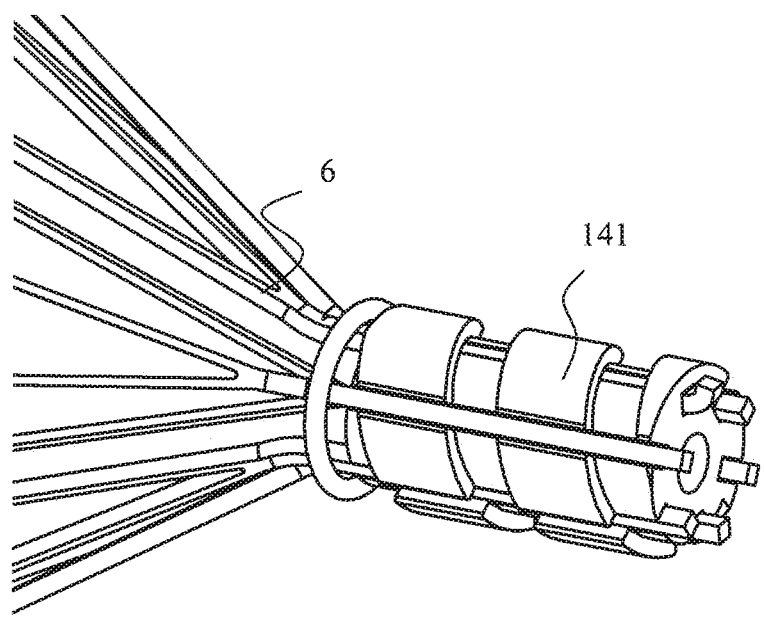
FIG. 29(h) is an isometric view of a vascular filter part of another vascular filter system according to the invention.
Figure 29I:
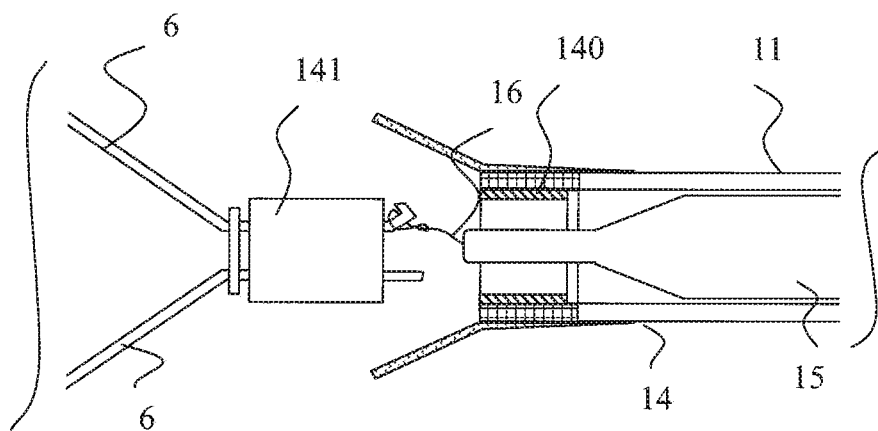
FIG. 29(i) is a cross sectional side view of the vascular filter system according to the invention in use.
Figure 29J:
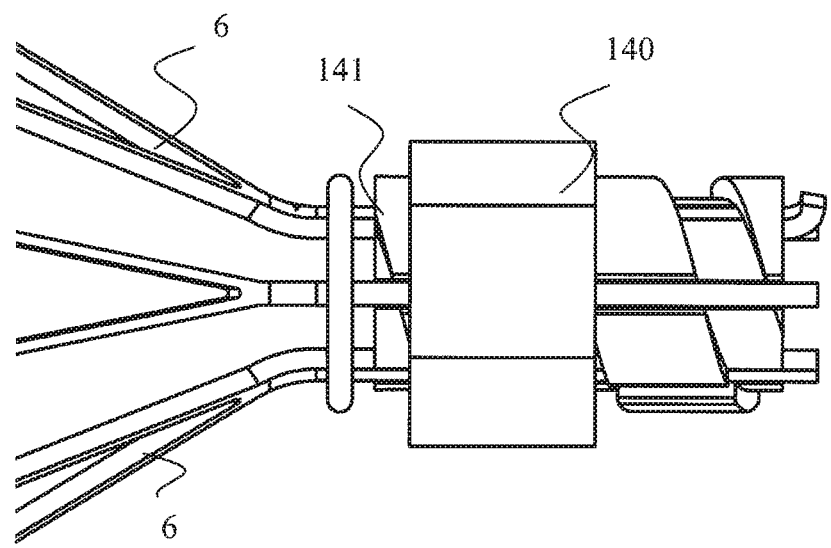
FIG. 29(j) is a side view of the vascular filter system of FIG. 29(i)
Figure 29K:
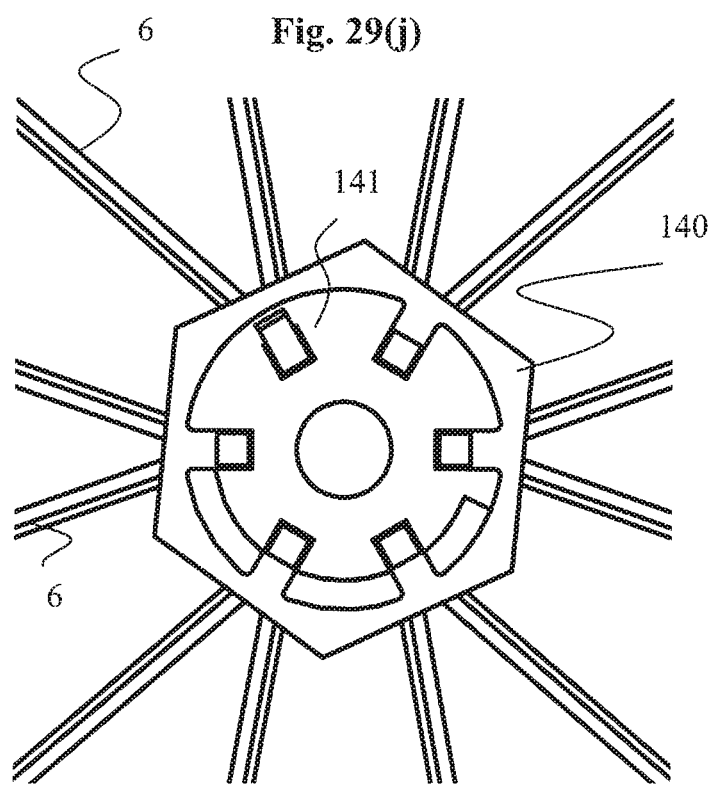
FIG. 29(k) is an end view of the vascular filter system of FIG. 29(i)
Figure 29L:
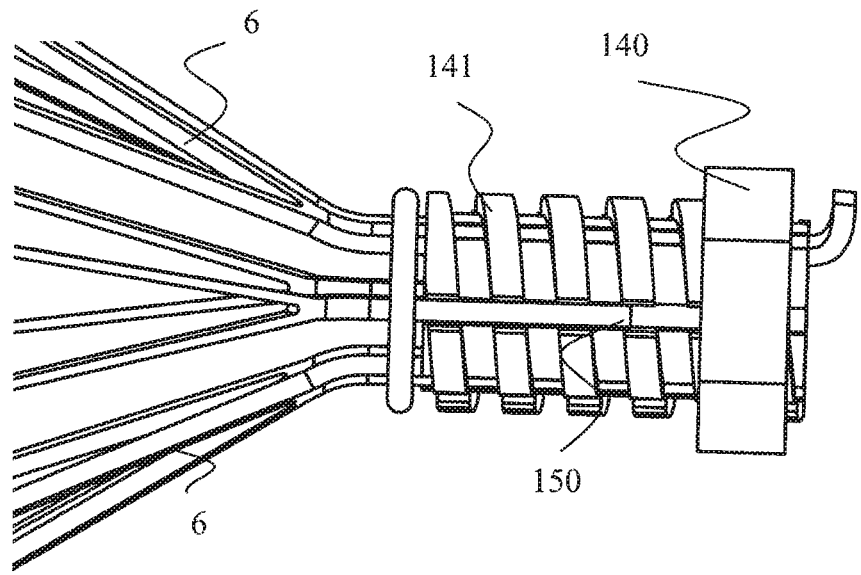
FIG. 29(l) is a side view of another vascular filter system according to the invention in a non-retaining configuration.
Figure 29M:
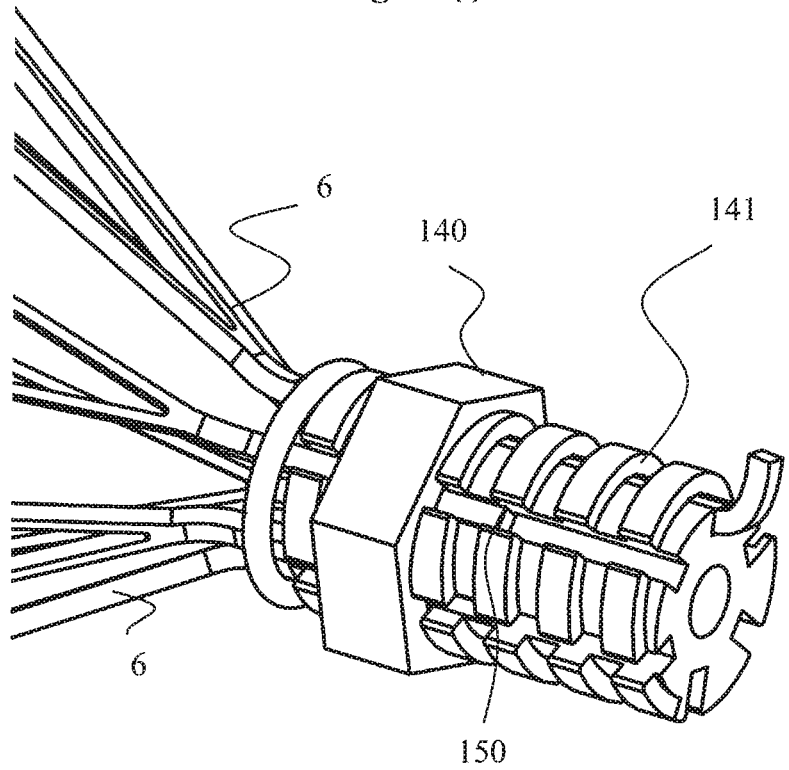
FIG. 29(m) is an isometric view of the vascular filter system of FIG. 29(l) in a retaining configuration.
Figure 29N:
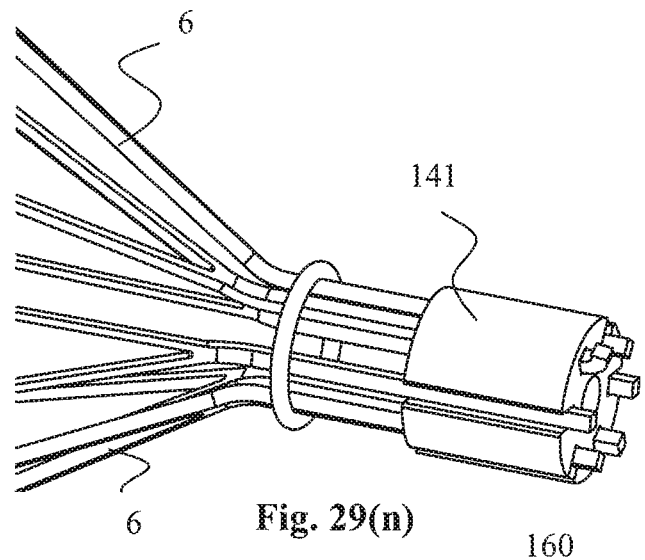
FIG. 29(n) is an isometric view of a vascular filter part of another vascular filter system according to the invention.
Figure 29O:
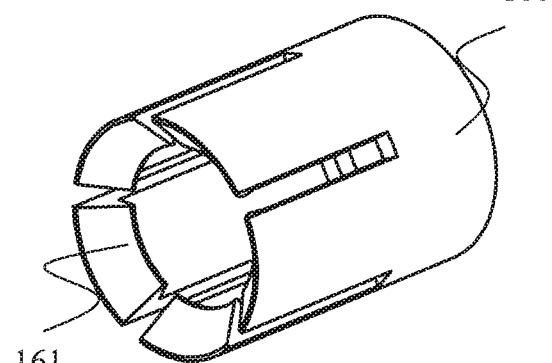
FIG. 29(o) is an isometric view of a retaining means part of the vascular filter system according to the invention.
Figure 29P:
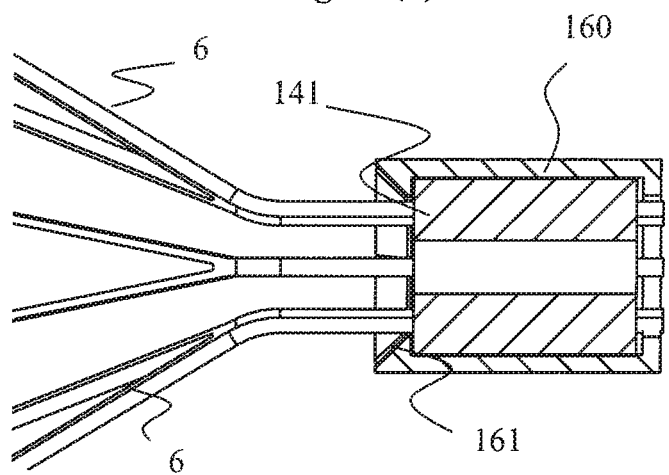
FIG. 29(p) is a cross sectional side view of the vascular filter part of FIG. 29(n) and the retaining means part of FIG. 29(o), FIGS. 30 to 32 are views similar to FIGS. 11 to 13(b) of another vascular filter system according to the invention in use.

In this case the retainer 40 is provided in the form of a clamp tube. The clamp tube has the same configuration both during delivery (FIG. 26) and during retaining (FIG. 29).

Figure 28:
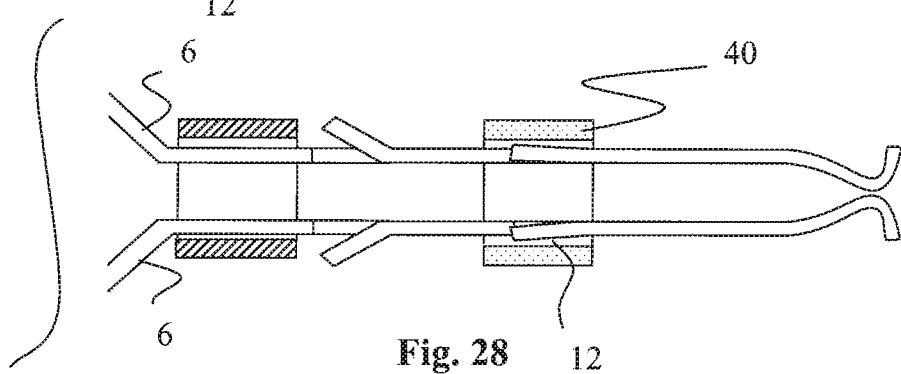

As illustrated in FIG. 28, the lips 12 are deformable to facilitate location of the clamp tube 40 around the distal ends of the filter elements 6 of the filter 1.

Figure 27:
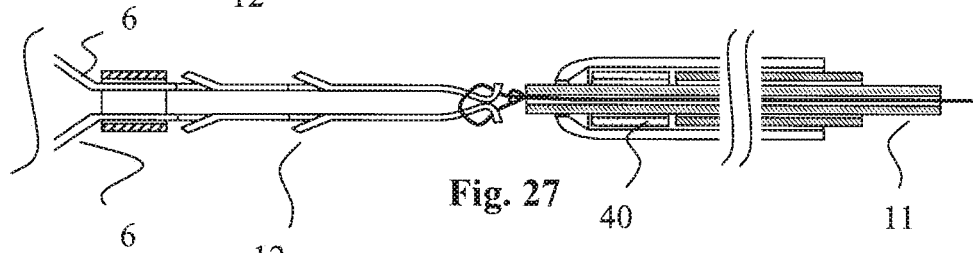

The grasping wire 16 may be used to maintain the position of the filer 1 relative to the inferior vena cava 2 during delivery of the clamp tube 40. In use, the grasping wire 16 is looped around the distal ends of the filter elements 6 of the filter 1 to hold the filter 1 relative to the delivery catheter 11 and to maintain the position of the filter 1 relative to the inferior vena cava 2 (FIG. 27). In order to prevent the support rings 3, 4 and barbs from being pulled distally or pushed proximally or vice versa depending on the direction of approach of the delivery catheter 11, the delivery mechanism 11 is provided in such a way as to balance the forces applied to the filter elements 6. For example, when pushing the clamp tube 40 over the apex endings, a simultaneous pull force is applied to the hook integral with the filter elements 6. The push force is applied with the pusher 13, and the pull force is applied with the snare 16. This force balancing may be incorporated into any of the embodiments disclosed herein from a proximal or distal approach. This arrangement prevents damage to the vessel wall during application of the secondary restraint 40.

The snare/lasso 16 is threaded over the distal books and tightened (FIG. 27). This centres the conversion catheter assembly 11 and holds the implant filtration elements 6 stationary while the biodegradable conversion ring 40 is translated over the retainers 12. Once tightened, the proximal end of the snare 16 and the snare outer tube 14 are held stationary while the pusher 13, and the extension ring 40 are advanced until the extension ring 40 is locked in position between the two sets of retainers 12.

The tip of the outer sheath 14 may encompass an expandable tip that allows the extension ring 40 to be advanced through it with force but not without force. This serves as a safety feature preventing the extension ring 40 from being detached prematurely.

The invention enables the filter 1 to be converted into a permanent filter if the indications for the patient changed or were incorrectly assessed at the time of implant. A means of achieving this is to use a catheter to place a cap, tie or other locking mechanism at the apex 7 of the filter 1 to hold the convertible filter elements 6 in the filter configuration permanently. This may be achieved using the catheter 11 which gains access to the venous system by percutaneous access and delivers the locking mechanism 40 to the filter site.

The hook is incorporated into the apex region 7 which may be engaged with the snare component 16 that is delivered from the distal side of the filter 1 (FIGS. 26 to 29). Snaring the hook allows the catheter 11 to be positioned accurately at the apex 7 of the filter 1. The catheter 11 houses the fixing component 40 to convert the filter 1 into a permanent device.

Once the hook is engaged and the snare 16 retracted, the outer tube 14 can be slid over the apex region, this will ensure good alignment and minimise any risk of the fixing component 40 becoming an embolus. The fixing component 40 is then pushed forward and released so that it engages the apex region 7 of the filter 1 constraining the filter elements 6 of the device 1 so that they cannot return to the vessel wall. The distal end of the apex region 7 includes the feature 12 that prevents the fixing component 40 moving distally.

In order for the fixing component 40 to engage in its final position it needs to navigate past this feature 12. This could be achieved by designing the component 40 to be held at a larger diameter in the catheter 11 but once it is released it springs back to a smaller diameter engaging with the filter 1 sufficiently to achieve a permanent attachment. Means of achieving this could be by using a coiled spring, a lattice or trellis type arrangement, or by using a slit tube. The fixing device 40 may also be inherently flexible to be pushed over the snap fit feature 12 into its final position.

FIGS. 29(*a*) to 29(*d*) illustrate another vascular filter system according to the invention, which is similar to the vascular filter system of FIGS. 26 to 29, and similar elements in FIGS. 29(*a*) to 29(*d*) are assigned the same reference numerals.

In this case each filter element 6 comprises a finger 121 protruding radially inwardly.

In the retaining state the clamp tube 120 extends around the fingers 121 of the filter elements 6 of the filter 1 to retain the filter 1 in the closed state (FIG. 29(*c*)) beyond elapse of the predetermined period of time. In particular, in the retaining state the clamp tube 120 engages with the fingers 121 of the filter elements 6 to clamp the filter 1 in the closed state. In the retaining state the clamp tube 120 is located in the region of the apex 7 of the filter 1 at the centre of the filter 1. The clamp tube 120 is located radially inwardly of the filter elements 6 of the filter 1 (FIG. 29(*c*)). The filtration arms 6 extend along the outer surface of the internal restraint 120.

Because of the presence of the clamp tube 120, the filter elements 6 are no longer free to move from the closed state to the open state upon elapse of the predetermined period of time. Upon biodegrading/bioabsorbing of the holder 122, the filter elements 6 of the filter 1 are retained in the closed state by the clamp tube 120 (FIG. 29(*d*)). In this manner the period of time in which the filter 1 captures thrombus is extended either temporarily or permanently.

As illustrated in FIG. 29(*b*), the lips 12 are deformable to facilitate location of the clamp tube 120 around the fingers 121 of the filter elements 6 of the filter 1.

Referring to FIGS. 29(*e*) to 29(*g*) there is illustrated another vascular filter system according to the invention, which is similar to the vascular filter system of FIGS. 29(*a*) to 29(*d*), and similar elements in FIGS. 29(*e*) to 29(*g*) are assigned the same reference numerals.

In this case the lips 12 are deformable to facilitate location of the clamp tube 130 around the fingers 121 of the filter elements 6 of the filter 1, and to facilitate selective removal of the clamp tube 130 from the fingers 121.

The clamp tube 130 comprises an engagable protrusion 131 around which the grasping wire 16 may be looped to assist removal of the clamp tube 130 from the fingers 121.

To remove the clamp tube 130 from the fingers 121, the grasping wire 16 is looped around the protrusion 131 (FIG. 29(*f*)). The grasping wire 16 is moved proximally relative to the filter 1 to draw the clamp tube 130 proximally causing deformation of the lips 12 (FIG. 29(*g*)), and removal of the clamp tube 130 from the fingers 121.

The proximal hook 131 is integral with the secondary restraint 130 and facilitates removal of the permanent/bioresorbable secondary restraint 130 when the need for filtration ceases.

In FIGS. 29(*h*) to 29(*k*) there is illustrated another vascular filter system according to the invention, which is similar to the vascular filter system of FIGS. 26 to 29, and similar elements in FIGS. 29(*h*) to 29(*k*) are assigned the same reference numerals.

In this case the filter 1 comprises a threaded docking member 141 at the distal end of the filter 1. The clamp tube 140 is also threaded. The docking member 141 is engagable with the clamp tube 140 by means of the threaded formations to releasably couple the clamp tube 140 in position around the distal ends of the filter elements 6 of the filter 1 (FIG. 29(*j*)). The threaded nature of the docking member 141 and the clamp tube 140 facilitates selective removal of the clamp tube 140 from the distal ends of the filter elements 6 of the filter 1.

In this thread arrangement the nut 140 is employed to extend the period of protection. The nut 140 may be in place upon initial intervention or attached at the time of extension.

The apex arms 6 are retained for the initial period of protection by the bioresorbable coupling means. The apex arms 6 are passed through slots in the biostable tube 141 with an outer thread. One of the slots is closed. The apex arm 6 extending through the closed slot is formed into a lip to hold the threaded tube 141 in place. Upon elapse of the predetermined protection period, the bioresorbable coupling means breaks and the capture and apex arms 6 revert to their radially biased state. The biostable tube 141 is retained on the apex arm 6 with the lip and becomes endotheliased at the vessel wall. Alternatively if the need for protection persists, the bioresorbable or biostable nut 140 may be threaded over the biostable tube 141 to extend the period of protection. If a biostable nut 140 is used, it is possible to remove the nut 140 by means of a retrieval system.

The nut 140 may be delivered to the device 1 by means of the catheter system 11. The catheter 11 encompasses a funnel, the centering nose 15, the snare 16, and the outer sheath 14 with a socket to assist in threading the nut 140 over the threaded tube 141.

FIGS. 29(*l*) and 29(*m*) illustrate another vascular filter system according to the invention, which is similar to the vascular filter system of FIGS. 29(*h*) to 29(*k*), and similar elements in FIGS. 29(*l*) and 29(*m*) are assigned the same reference numerals.

In this case the clamp tube 140 is movable proximally from a non-retaining position (FIG. 29(*l*)) to a retaining position (FIG. 29(*m*)) by rotating the clamp tube 140 relative to the docking member 141.

In the non-retaining position the clamp tube or nut 140 is mounted to the docking member 141 distally of the distal end 150 of each of the filter elements 6 of the filter 1. In the non-retaining position the filter 1 is not retained in the closed state by the clamp tube 140.

In the retaining position the clamp tube 140 is mounted to the docking member 141 proximally of the distal end 150 of each of the filter elements 6 of the filter 1. In the retaining position the filter 1 is retained in the closed state by the clamp tube 140. The clamp tube 140 extends around the filter elements 6 of the filter 1 to retain the filter 1 in the closed state beyond elapse of the predetermined period of time. In particular, in the retaining position the clamp tube 140 engages with the filter elements 6 of the filter 1 to clamp the filter 1 in the closed state.

The nut 140 is preloaded on the biostable tube 141. The threaded tube 141 extends distally of the apex arms 6 so that the preloaded nut 140 does not retain the apex arms 6 (FIG. 29(*l*)).

The nut 140 may be in the form of a common hexagonal nut or it may be a custom shape with features engagable with a custom designed socket.

Referring to FIGS. 29(*n*) to 29(*p*) there is illustrated another vascular filter system according to the invention, which is similar to the vascular filter system of FIGS. 29(*h*) to 29(*k*), and similar elements in FIGS. 29(*n*) to 29(*p*) are assigned the same reference numerals.

In this case the docking member 141 is not threaded. The clamp tube 160 is also not threaded. An inwardly protruding lip 161 is provided at the proximal end of the clamp tube 160. The docking member 141 is engagable with the clamp tube 160 in a snap-fit manner by means of the lip 161 to couple the clamp tube 160 in position around the distal ends of the filter elements 6 of the filter 1 (FIG. 29(*p*)).

The snap fit biostable restraint 160 is translated over the pre-loaded biostable tube 141 with slots for the apex arms 6. One of the slots is closed.

In another embodiment, a secondary retaining ring may be deployed from the proximal end into a snap fit arrangement integral with the filter apex. A proximal hook may be used to aid in grasping the filter 1 to locate the secondary restraint.

FIGS. 30 to 37 illustrate a further vascular filter system according to the invention, which is similar to the vascular filter system of FIGS. 1 to 18, and similar elements in FIGS. 30 to 37 are assigned the same reference numerals.

In this case the retainer 50 is provided in the form of a clamp device. The clamp device 50 comprises a plurality of arms ill. The clamp device 50 is movable between an open state (FIG. 36) and a closed retaining state (FIG. 37) by operation of the delivery catheter 51.

Figure 33:
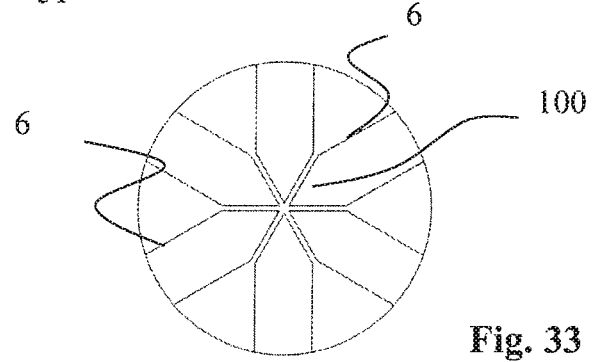
FIG. 33 is an end view of a vascular filter part of the vascular filter system of FIGS. 30 to 32, FIGS. 34 to 37 are views similar to FIGS. 11 to 13(b) of a retaining means part of the vascular filter system of FIGS. 30 to 32 in use.
Figure 34:
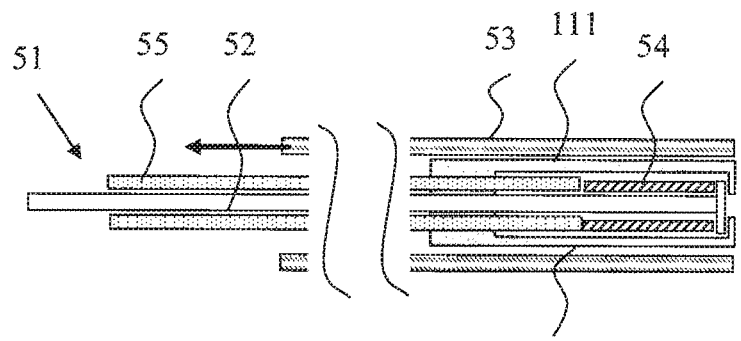

As illustrated in FIG. 33, the twelve filter elements 6 are arranged into six pairs. For each pair, the distal tip of one filter element 6 is attached to the distal tip of the other filter element 6. In this manner a loop opening 100 is formed between each pair of filter elements 6.

In the retaining state the arms 111 of the clamp device 50 extend through the loop openings 100 between adjacent filter elements 6 of the filter 1 to retain the filter elements 6 of the filter 1 in the closed state (FIG. 32) beyond elapse of the predetermined period of time. In particular, in the retaining state the clamp device 50 engages with the filter elements 6 of the filter 1 to clamp the filter 1 in the closed state. The clamp device 50 is located in the region of the apex 7 of the filter 1 at the centre of the filter 1.

The delivery catheter 51 is employed to deliver the clamp device 50 to the filter 1 after the filter 1 has been deployed in the inferior vena cava 2. The delivery catheter 51 comprises an inner tube 52, an outer sheath 53, and an expandable member 54 at the distal end of an intermediate tube 55 upon which the clamp device 50 is mounted.

It will be appreciated that in the retaining state the arms 111 of the clamp device 50 may alternatively extend through an opening in a filter element 6 of the filter 1 to retain the filter elements 6 of the filter 1 in the closed state beyond elapse of the predetermined period of time.

Figure 30:
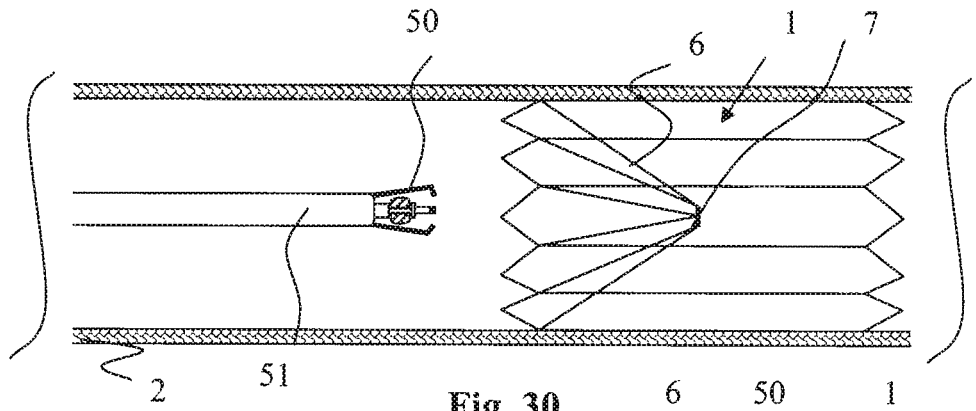
Figure 35:
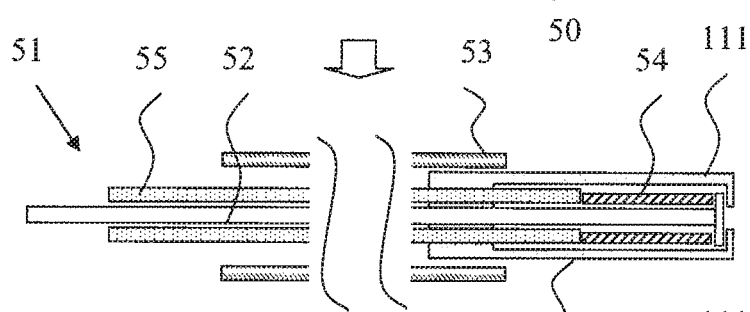
Figure 36:
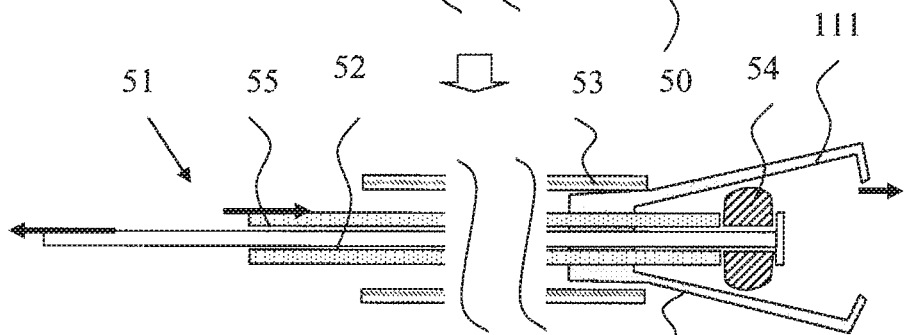

In use, the clamp device 50 is mounted on the intermediate tube 55 of the delivery catheter 51. The delivery catheter 51 is advanced through the inferior vena cava 2 until the clamp device 50 reaches the distal ends of the filter elements 6 of the filter 1, which has previously been deployed in the inferior vena cava 2 (FIG. 30). The outer sheath 53 is retracted to uncover the clamp device 50 (FIG. 35). The inner tube 52 is moved proximally relative to the intermediate tube 55 to expand the expandable member 54 thereby moving the clamp device 50 from the closed retaining state to the open state (FIG. 36).

Figure 31:
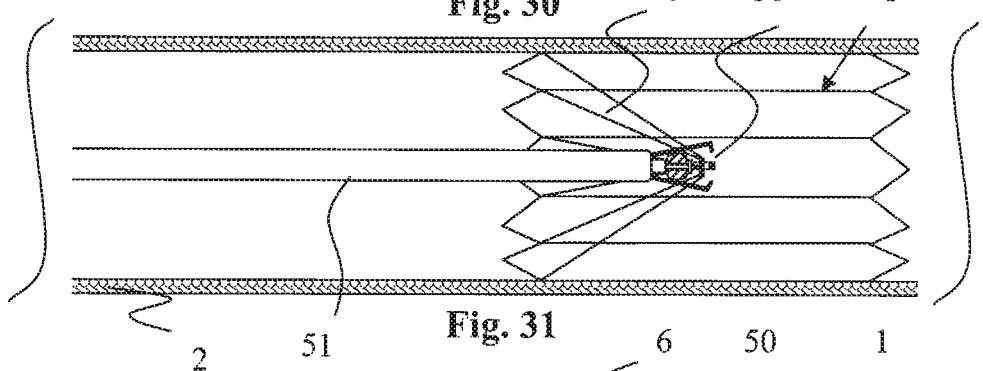
Figure 32:
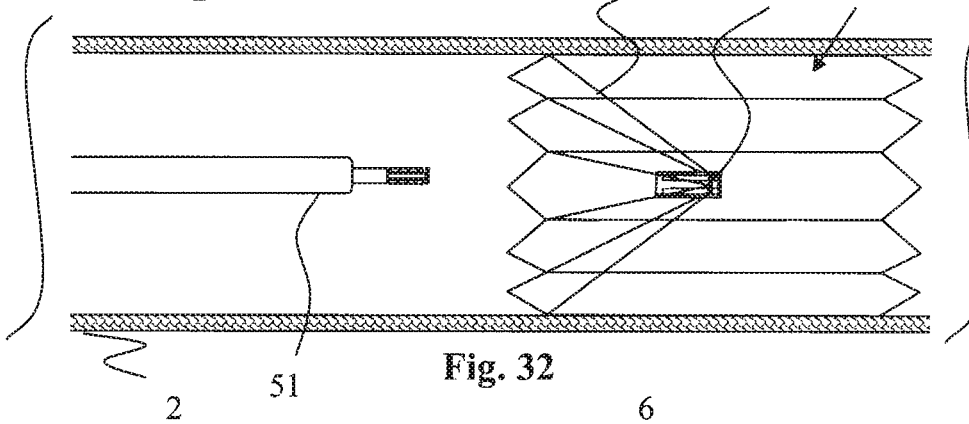
Figure 37:
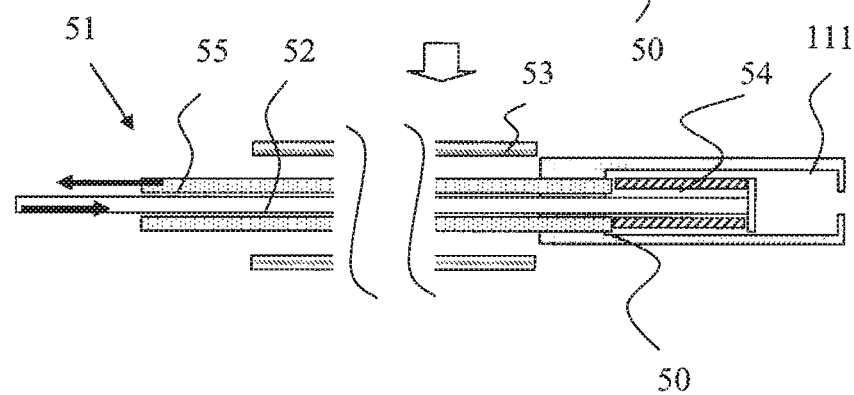
FIG. 37(a) is an isometric view of a retaining means part of another vascular filter system according to the invention.
Figure 37A:
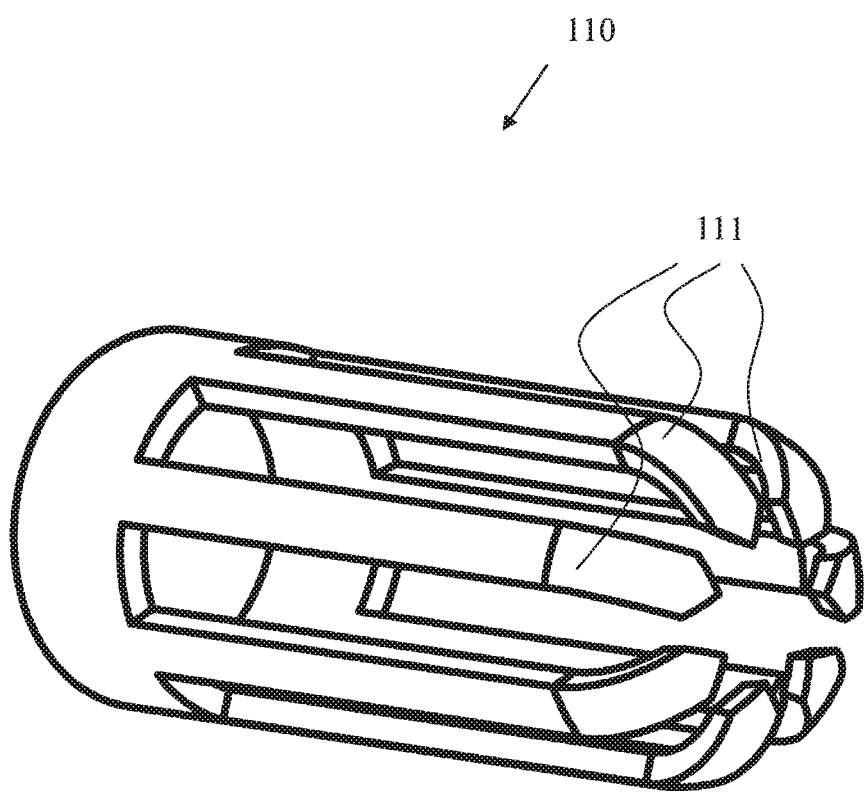

The delivery catheter 51 is advanced further through the inferior vena cava 2 until the arms 111 of the clamp device 50 extend through the loop openings 100 between adjacent filter elements 6 of the filter 1 (FIG. 31). The inner tube 52 is moved distally relative to the intermediate tube 55 to contract the expandable member 54 thereby moving the clamp device 50 from the open state to the closed retaining configuration (FIG. 37). In the retaining state the clamp device 50 engages with the filter elements 6 of the filter 1 to clamp the filter 1 in the closed state beyond elapse of the predetermined period of time (FIG. 32). Upon elapse of the predetermined period of time the holder biodegrades/bioabsorbs. The filter elements 6 of the filter 1 are retained in the closed state by the holder clamp device 50. In this manner the period of time in which the filter 1 captures thrombus is extended either temporarily or permanently.

As illustrated in FIG. 32, the claw type device 50 may be used to restrain the filtration elements 6 from opening. For insertion through the loops 100 of the filtration elements 6, the claw 50 is opened through shape memory or mechanical actuation, after which the claw 50 reverts to its closed state. The closed state may be achieved through shape memory properties or mechanical actuation. The proximal end of the claw 50 may encompass a conical, spherical, or parabolic geometry in order to minimise stagnant areas and resistance to blood flow.

The vena cava filter 1 has the device 50 which can be used to change the filter 1 into a permanent filter if the indications of the patient changed or were incorrectly assessed at the time of implantation. A means of achieving this would be to use the catheter 51 to place a cap, tie or other locking mechanism at the apex 7 of the filter 1 to hold the absorbable filter elements 6 in the filter configuration permanently. This could be achieved using the catheter 51 which gains access to the venous system by percutaneous access and delivers the locking mechanism 50 to the filter site.

FIGS. 30 to 32 show the means of doing this using the grabbing type component 50. The internal push rod 55 is advanced releasing the grabbing component 50 which was constrained in the sheath 53. The grabbing component 50 has arms which engage with the filter frame 6 when advanced. The grabbing component 50 is then deformed back to a reduced diameter using the external tube or sheath 53.

As illustrated in FIG. 33, at the apex region 7 the neighbouring filter elements 6 are close or touching ensuring that the arms of the grabbing component 50 engage within the filter element 6 rather than through neighbouring elements 6. The filtration elements 6 may be arranged to prevent the grabber 50 engaging between filtration elements 6.

It may be possible to convert the filter 1 to a permanent filter from either the proximal or distal side facilitating an access route from the femoral or jugular vein. The claw 50 may be advanced from a proximal or distal approach. Opening of the claw 50 may be achieved mechanically through compression of the tube or ring of material 54. Upon compression, the tube/ring 54 expands radially, thus opening the claw 50. Once in position, the claw 50 is closed through release of the compressive force. To achieve the closing mechanism, the claw 50 may be manufactured from a shape memory or spring material.

The number of arms 111 of the clamp device may be varied as appropriate. For example the clamp device 110 of FIG. 37(*a*) comprises seven arms 111, and is suitable for use with the six pairs of filter elements 6. By including more arms 11 on the clamp device 110 than loop openings 100 between the filter elements 6, this results in a degree of redundancy to ensure that the arms 111 of the clamp device 110 will extend through the loop openings 100 to safely retain the filter elements 6 of the filter 1 in the closed state. Only one claw 111 needs to extend through a pair of joined filter elements 6. The seven prong claw 110 will always catch with the filter 1 comprising six joined filter element pairs.

Referring to FIGS. 38 to 42 there is illustrated another vascular filter system according to the invention, which is similar to the vascular filter system of FIGS. 1 to 18, and similar elements in FIGS. 38 to 42 are assigned the same reference numerals.

In this case a retainer 60 is provided in the form of a tie element to tie the filter elements 6 of the filter 1 in the closed state beyond elapse of the predetermined period of time. The tie element 60 is of a flexible material that may be knotted. The tie element 60 is movable between an open delivery configuration (FIG. 39) and a closed retaining configuration (FIG. 41).

The delivery catheter 61 is employed to deliver the tie element 60 to the filter 1 after the filter 1 has been deployed in the inferior vena cava 2.

The lasso 60 may be used to extend protection permanently/temporarily. The lasso 60 is advanced within the deployment catheter 61 from a proximal or distal approach. When it has engaged with the ends of the filtration elements 6, it is tightened and detached from the catheter 61.

The filter 1 may be changed into a permanent filter if the indications of the patient changed or were incorrectly assessed at the time of implant. A means of achieving this would be to use the catheter 61 to place a cap, tie or other locking mechanism at the apex 7 of the filter 1 to hold the absorbable filter elements 6 in the closed, capturing, state permanently. This could be achieved using the catheter 61 which gains access to the venous system by percutaneous access and delivers the locking mechanism 60 to the filter 1.

To retain the tie 60 or cap at the apex region 7, the elements 6 are extended past the apex point 7.

The retainer 60 may be provided in the form of a helical coil or spring deployed from the catheter 61 to retrain the filter elements 6 from opening. Shape memory or spring materials may be used.

Figures 42, 43:
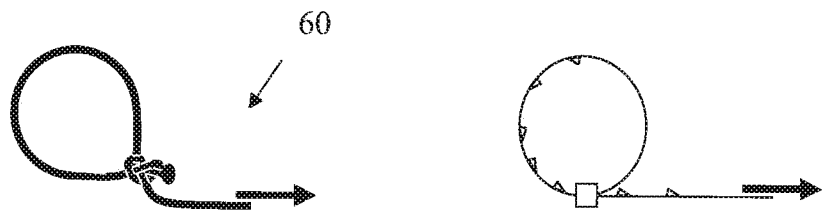
FIG. 42 is an isometric view of a retaining means part of the vascular filter system of FIGS. 38 to 41.
FIG. 43 is a side view of a retaining means part of another vascular filter system according to the invention.
Figure 44A:
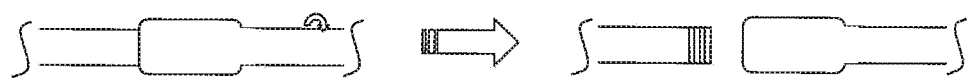
FIGS. 44(a) to 44(d) are side views of retaining means parts of other vascular filter systems according to the invention.
Figure 44B:
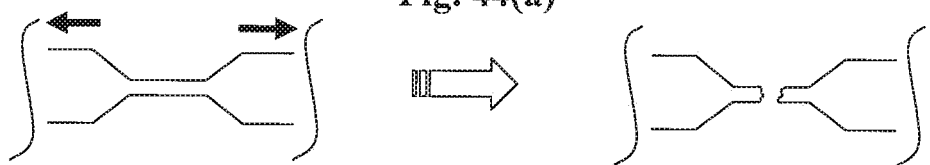
Figure 44C:
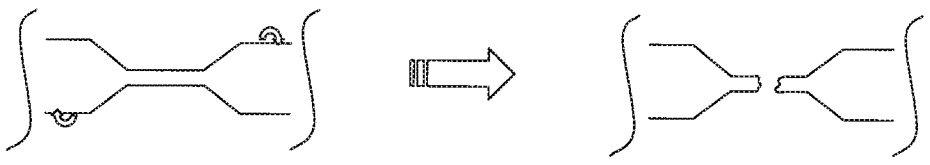
Figure 44D:
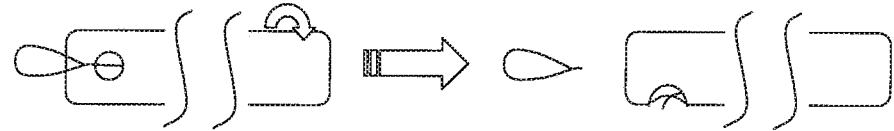

A potential means of doing this is by using the lasso type feature 60 which engages with the apex 7 of the filter 1 and is tightened to fix the filter 1 before the loop 60 is detached from the catheter 61. The loop 60 could be designed with ratchet type features so it locks in place when it is being tightened (FIG. 43). The taut loop 60 may be secured via a knot (FIG. 42) or ratchet lasso/loop system (FIG. 43). The taut secure loop/lasso 60 may be detached by a screw (FIG. 44(*a*)), by a mechanical cut (FIG. 44(*b*)), by shear load (FIG. 44(*c*)), or by a tensile load system. The loop/noose 60 could be detached using a screw attachment (FIG. 44(*a*)). Also a cutting mechanism may be designed into the catheter 61 to cut the noose (FIG. 44(*d*)). It is also envisaged to have a reduced cross section beside the detachment point and provide an electric current to break the wire.

The loop of material for the lasso 60 can be made such that it would be bioabsorbable/biodegradable and thus extend the duration that the filter 1 will remain in the closed configuration. Alternatively the material may be a biostable material such that the filter 1 will not convert at any time.

Figure 45:
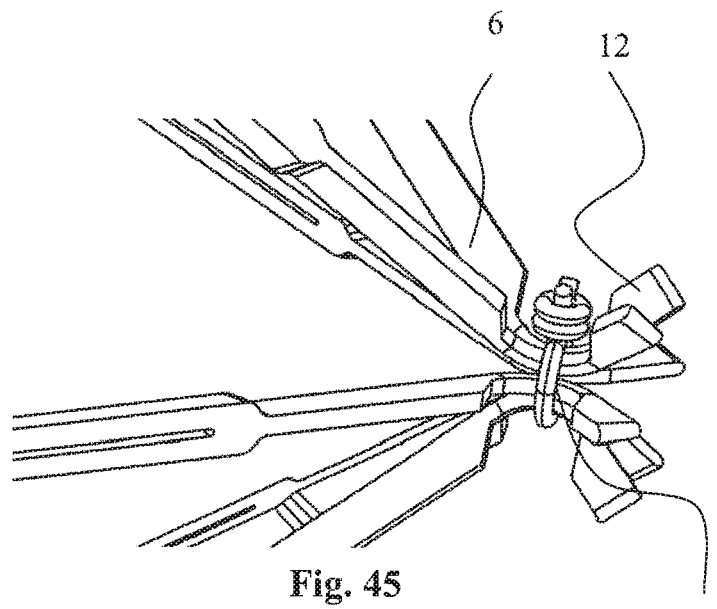
FIG. 45 is an isometric view of a vascular filter part of another vascular filter system according to the invention.
Figure 46:
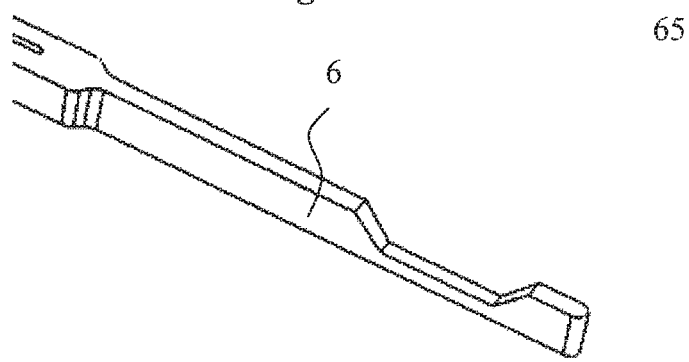
FIGS. 46 and 47 are isometric views of part of the vascular filter part of FIG. 45.
Figure 47:
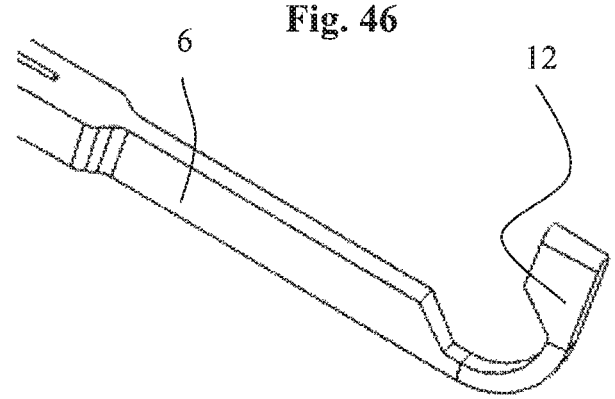

The lip 12 may be formed integrally in the filter element 6, as illustrated in FIGS. 45 to 49. A method of manufacturing the filter 1 is shown in FIGS. 45 to 49. Firstly a notch is machined in the strut 6 at the distal end of the filter 1 as shown in FIG. 46. The tip of the filter arm 6 is then heat-set in a shape similar to that shown in FIG. 47. FIG. 46 illustrates the strut 6 with the notch created, and FIG. 47 illustrates the strut 6 heat-set into position.

The filter element arms 6 may then be constrained together in the filtering closed state for the original period until elapse of the predetermined period of time using the holder 65 which may be provided in a variety of possible means, for example a piece of biodegradable suture tied at the ends. The holder 65 temporarily holds the filter elements 6 in the closed state until elapse of the predetermined period of time.

Figure 48:
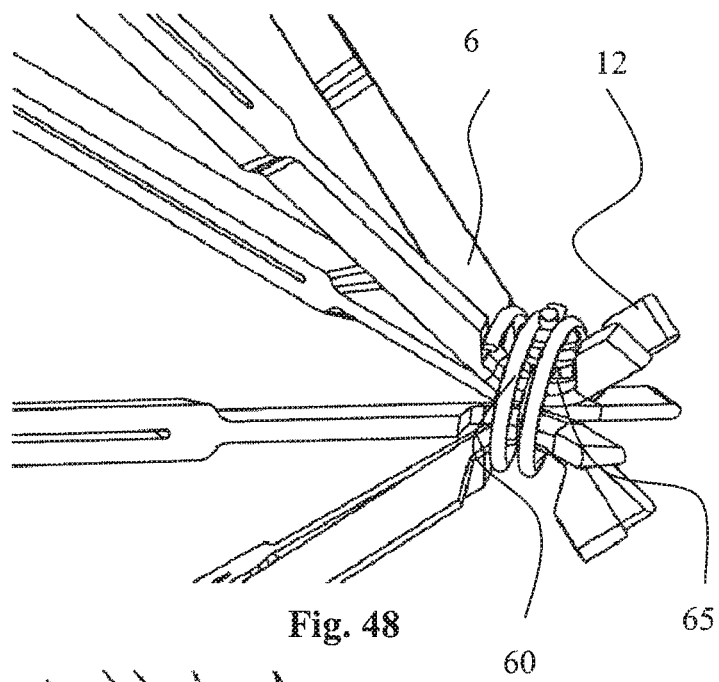
FIG. 48 is an isometric view of the vascular filter part of FIG. 45 and a retaining means part of the vascular filter system before elapse of a predetermined period of time.

The notches on the filter element arms 6 provide a suitable anchoring location for the biostable or biodegradable retainer loop 60 to be deployed over the biodegradable holder 65 around the tips 12 and tightened down to hold the filter elements 6 temporarily or permanently in the filtering configuration beyond elapse of the predetermined period of time (FIG. 48). The retainer 60 extends the period of filtration.

Figure 49:
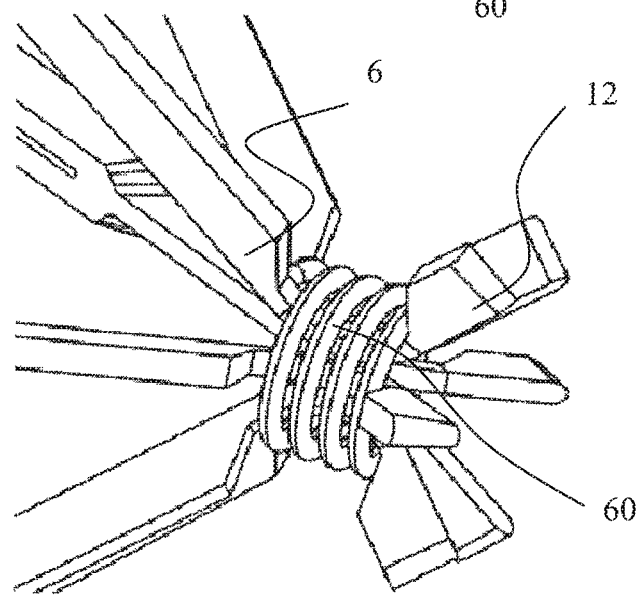
FIG. 49 is an isometric view of the vascular filter part of FIG. 45 and the retaining means part of FIG. 48 after elapse of the predetermined period of time.
Figure 50:
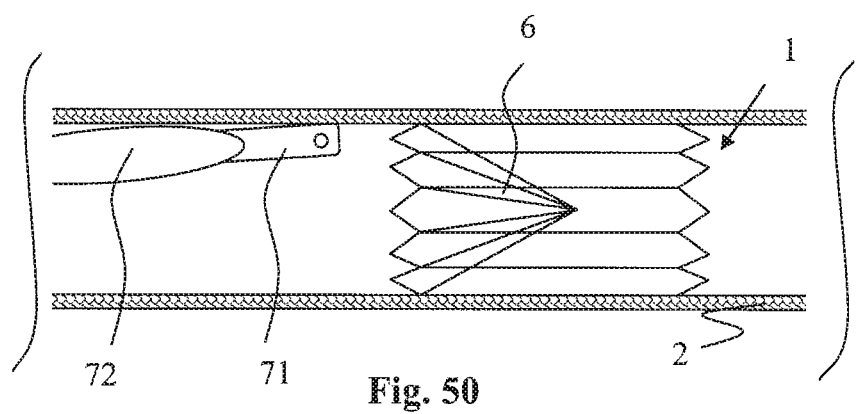
FIGS. 50 and 51 are views similar to FIGS. 11 to 13(b) of another vascular filter system according to the invention in use.

FIG. 45 illustrates the degradable holder 65 in place. FIG. 48 illustrates the secondary retainer 60 deployed over the primary holder 65. FIG. 49 illustrates the secondary retainer 60 after the primary holder 65 has bio-degraded/bio-absorbed.

It will be appreciated that a variety of types of tie element may be used to tie the filter elements 6 of the filter 1 in the closed state beyond elapse of the predetermined period of time.

It will be appreciated that a variety of types of retainer may be used to constrain the filter elements 6 of the filter 1 in the closed state beyond elapse of the predetermined period of time, for example a coil, loop, ring or cap.

In FIGS. 50 to 55 there is illustrated another vascular filter system according to the invention, which is similar to the vascular filter system of FIGS. 38 to 42, and similar elements in FIGS. 50 to 55 are assigned the same reference numerals.

In this case the tie element 70 is woven around and through the filter elements 6 to tie the filter elements 6 of the filter 1 in the closed state beyond elapse of the predetermined period of time.

The delivery catheter 71 is employed to deliver the tie element 70 to the filter 1. The delivery catheter 71 comprises an inflatable balloon 72 to assist in centering the delivery catheter 71 in the blood vessel 2 (FIG. 51).

Figure 51:
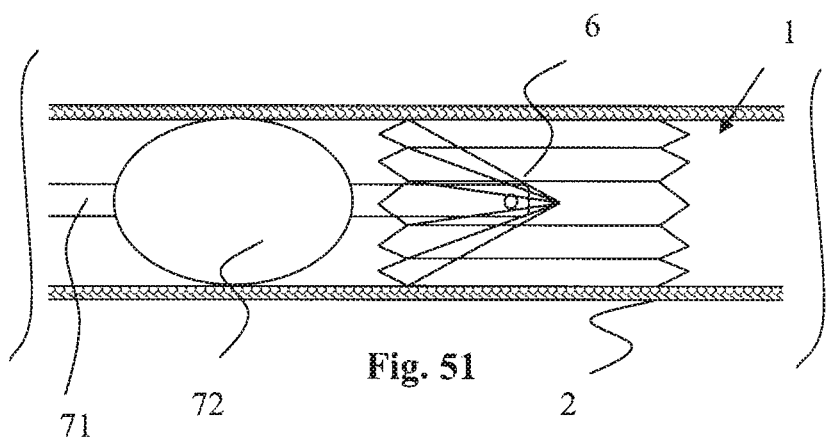

As illustrated in FIG. 51, the coil deployment catheter 71 is advanced to the site of the implant 1 via a proximal approach until the distal tip is centred in the vessel 2 by the conical shape of the implant filtration elements 6. The inflatable balloon 72 may be incorporated to aid centring of the catheter 71. The catheter 71 may also be advanced from a distal approach.

Figure 52:
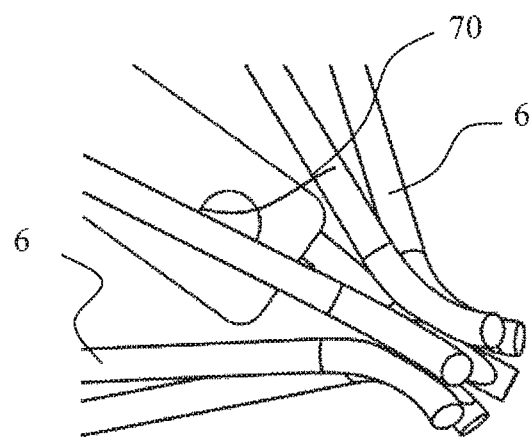
FIGS. 52 to 55 are isometric views of the vascular filter system of FIGS. 50 and 51 in use.
Figure 53:
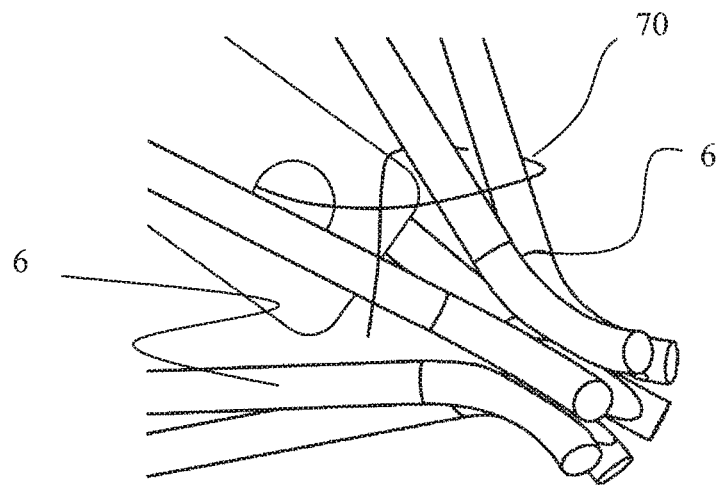
Figure 54:
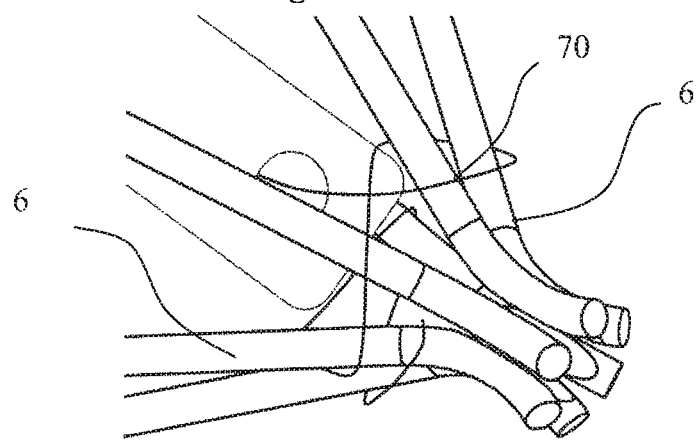
Figure 55:
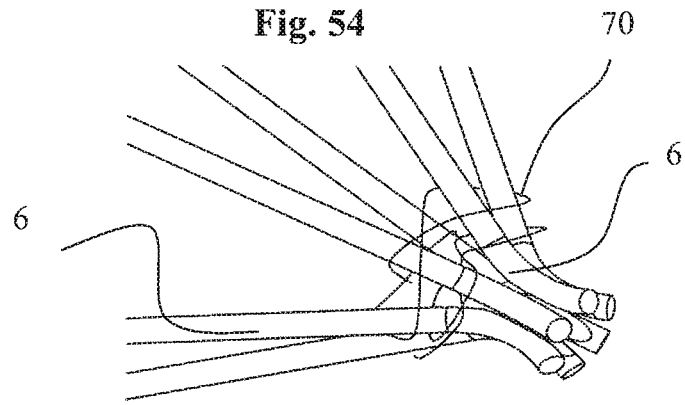

The coil 70 is preprogrammed through shape memory to change direction/orientation as a length of the coil 70 is deployed (FIG. 52). As the coil 70 changes direction, it winds itself in between the filtration elements 6 until a binding matrix is formed at the apex 7 of the filter portion. The coil matrix 70 restrains the filtration elements 6 from opening when the original biodegradable restraint finalises its degradation process. Once the coil 70 is deployed, the delivery catheter 71 is removed.

Figure 56:
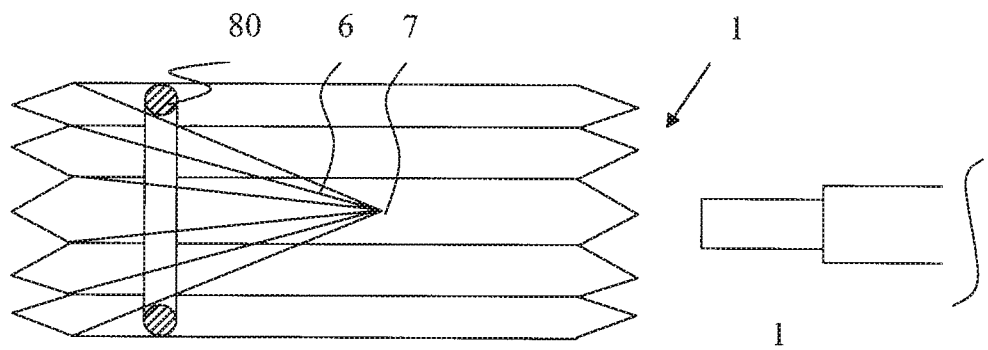
FIG. 56 is a cross sectional side view of another vascular filter system according to the invention.

FIG. 56 illustrates a further vascular filter system according to the invention, which is similar to the vascular filter system of FIGS. 1 to 18, and similar elements in FIG. 56 are assigned the same reference numerals.

In this case the retainer 80 is provided in the form of a support ring.

The support ring 80 extends around the proximal ends of the filter elements 6 of the filter 1 to retain the filter 1 in the closed state beyond elapse of the predetermined period of time. In particular, the support ring 80 engages with the filter elements 6 of the filter 1 to support the filter 1 in the closed state. The support ring 80 is located in the region of the end of the filter elements 6 opposite to the apex 7 of the filter 1 at the side of the filter 1.

The support ring 80 may be inflatable via hydrogel or saline, or may be a solid ring. The support ring 80 may be deployed from a catheter within the filter 1 to restrain the filtration elements 6 at the wall of the vessel 2, between the wall of the vessel 2, or at the central axis of the vessel 2.

Figure 57:
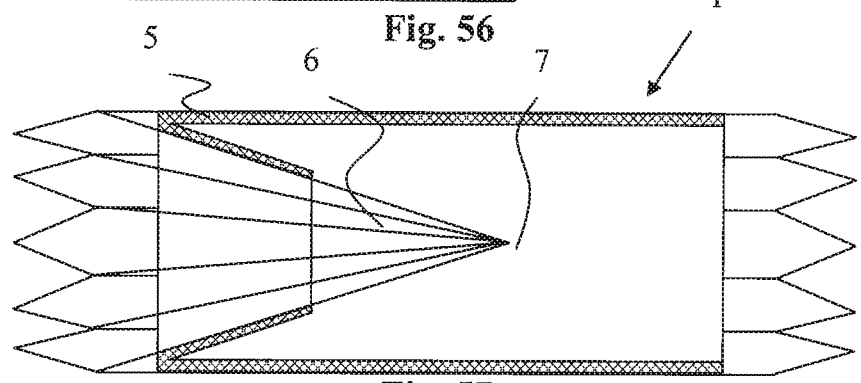
FIGS. 57 to 59 are views similar to FIG. 56 of other vascular filter systems according to the invention.
Figure 58:
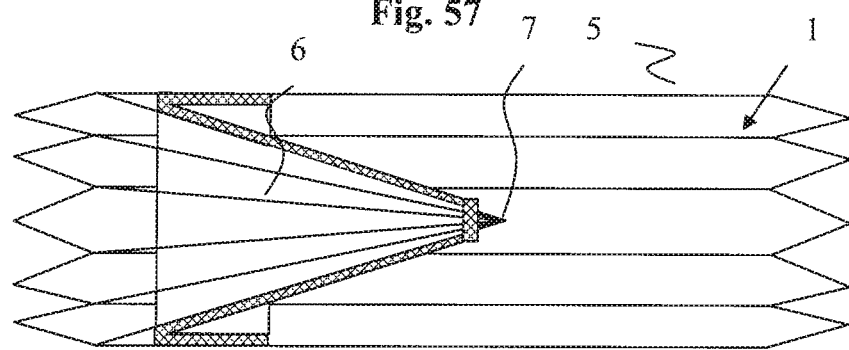
Figure 59:
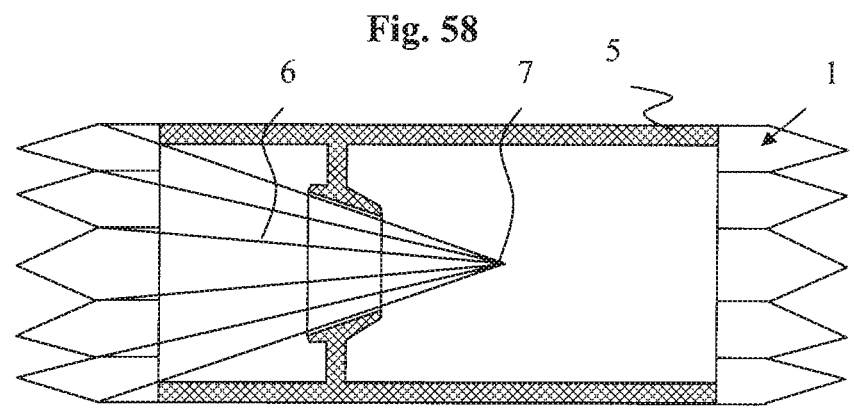

The location of the retainer relative to the filter 1 may be varied, as illustrated in FIGS. 57 to 59. The retainer may engage with the filter elements 6 of the filter 1 and/or with the support struts 5 of the filter 1 to support the filter 1 in the closed state. The retainer may extend along part or substantially all of the filter elements 6. The retainer may be located at any suitable point along the filter elements 6.

The restraining device may encompass supports extending distal and/or proximal of the restraint (FIG. 59). This support may be in the form of a tubular mesh.

Figure 62:
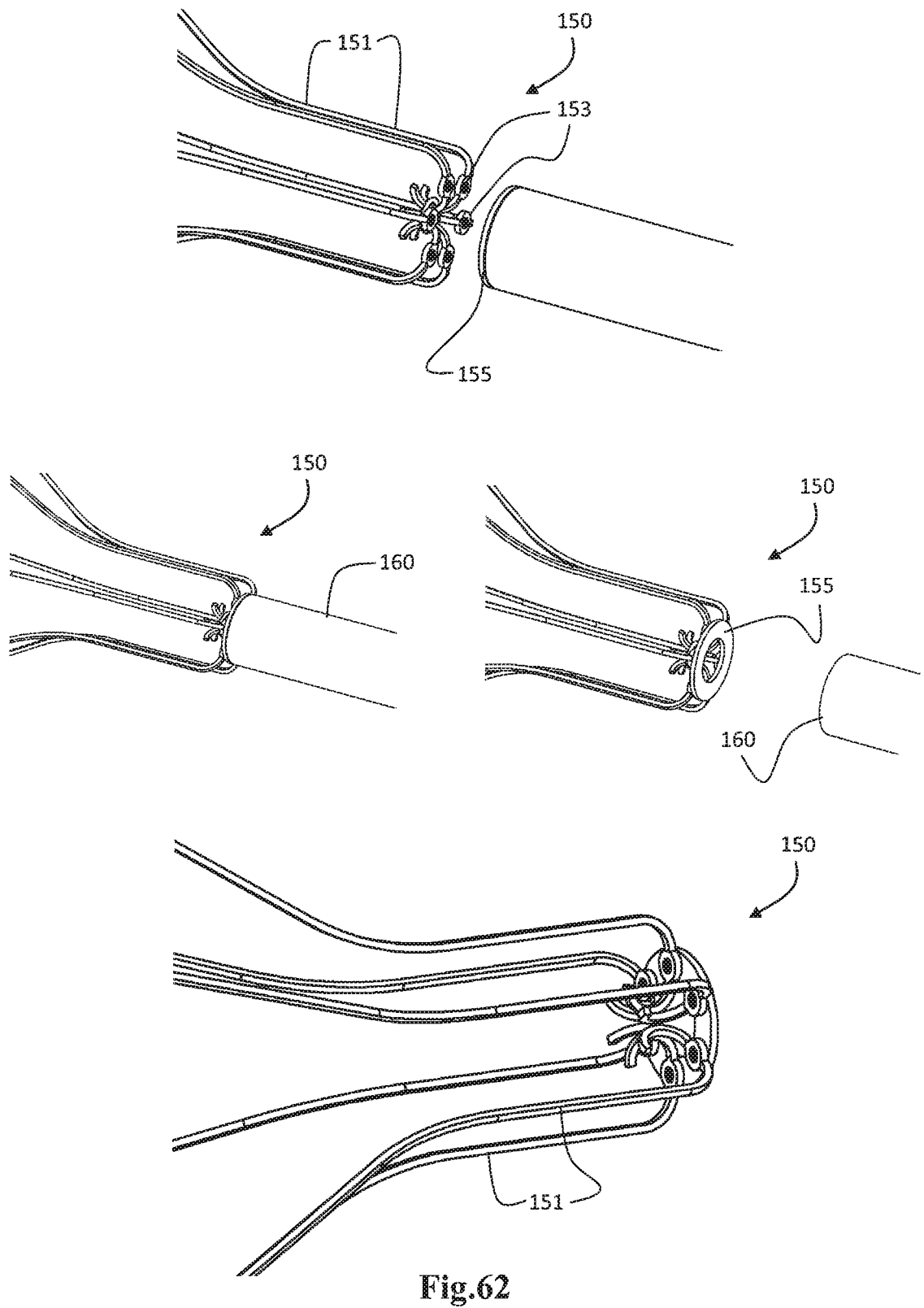
FIG. 62 shows delivery of the second retainer part.

Referring to FIGS. 60 to 62 a filter 150 has filter elements 151 which are curved inwardly and proximally at their distal ends. The filter elements 151 are held in the closed state by a biodegradable holder 152. Also, the filter elements 151 include retainer disc-shaped magnetic parts 153 located at the bends at the distal ends. The retainer also comprises a washer-shaped second part 155 which is delivered by a catheter 160 so that it engages the first magnetic parts 153. The complete retainer thereby holds the filter elements in the closed state (FIG. 62). In more detail the magnetic inserts 153 may be positioned by heating the filter elements and then cooling to secure the magnetic inserts 153. Alternatively, they could be bonded or crimped in place. The retainer second part 155 may be deployed without need for a snare or funnel guiding system, but these may be provided additionally if desired. During deployment of the retainer second part, the magnetic attraction between the part 155 and the filter elements is greater than that between the part 155 and the catheter. The retainer part 155 may be coupled to the catheter by an interference fit in place of or in addition to the magnetic attraction.

Figure 63:
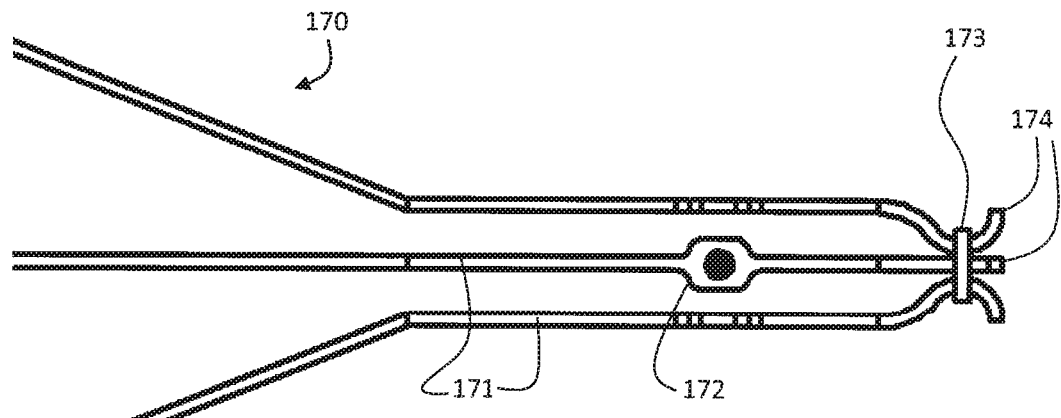
FIG. 63 is a side view of a further filter of the invention.
Figure 64:
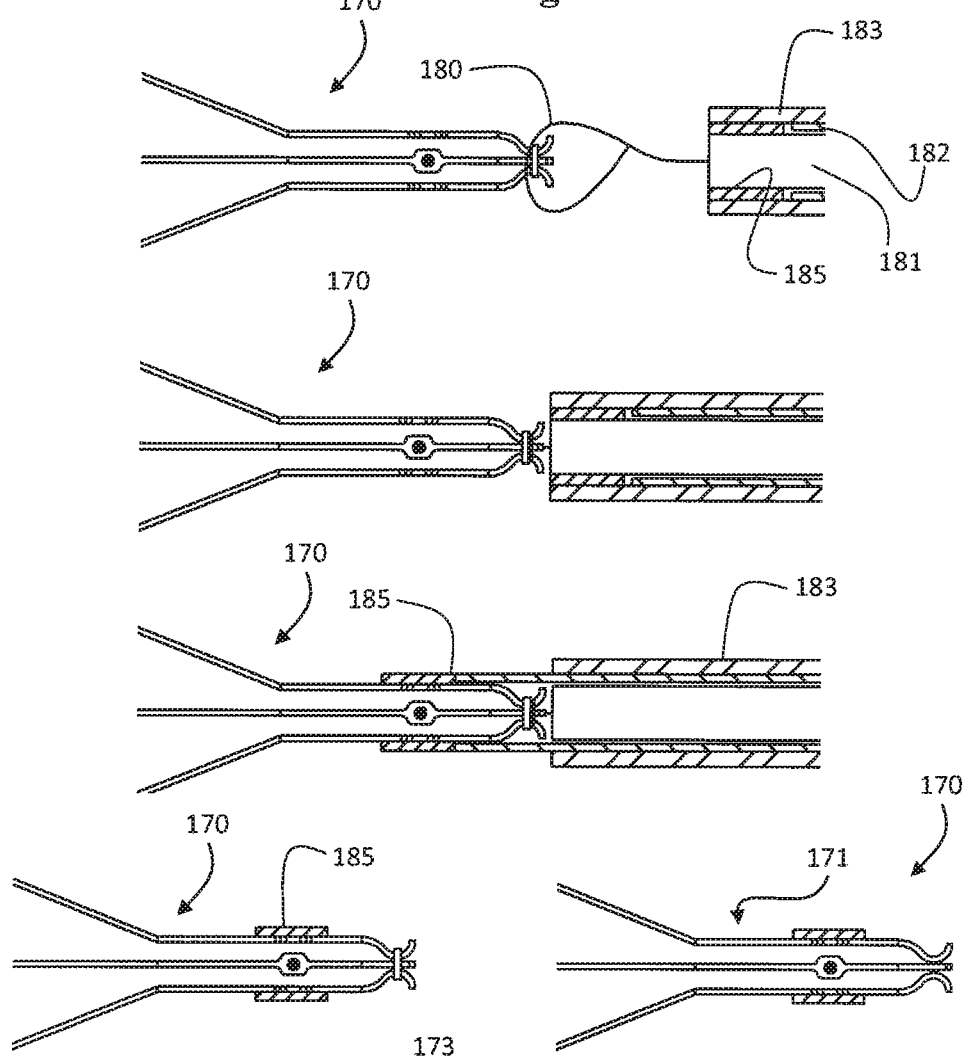
FIG. 64 shows delivery of a sleeve-shaped magnetic retainer by a catheter.

Referring to FIGS. 63 and 64 a filter 170 has filter elements 171 held for a predetermined period of time by a biodegradable holder 173. The filter elements 171 have bends at their distal ends, the bends being faced inwardly and the ends 174 of the elements 171 extending radially outwardly. Each filter element 171 has a retainer magnetic insert 172. To extend the protection period, the filter element hook ends are grasped with a snare 180 which is tightened to bring the apex and the catheter into close contact. The catheter central shaft 181 and sheath 183 are held stationary and a pusher 182 advances a magnetic collar 185 over the filter element magnets 172. The magnetic attraction forces prevent the collar 185 from slipping. The central shaft 181 may have a reception space for the filter element hook ends. The collar 185 is held in position in the delivery system by an interference fit or by a magnetic insert on the central shaft 181. Alternatively, the collar 185 may be attached to the pusher by magnetism. Of course, in order for the pusher to release the collar 185, the magnetic attraction force between the collar and the pusher should be less than that between the filter elements and the collar. The filter element ends may extend proximally in order for the extension step to be performed from a femoral approach.

Figure 65:
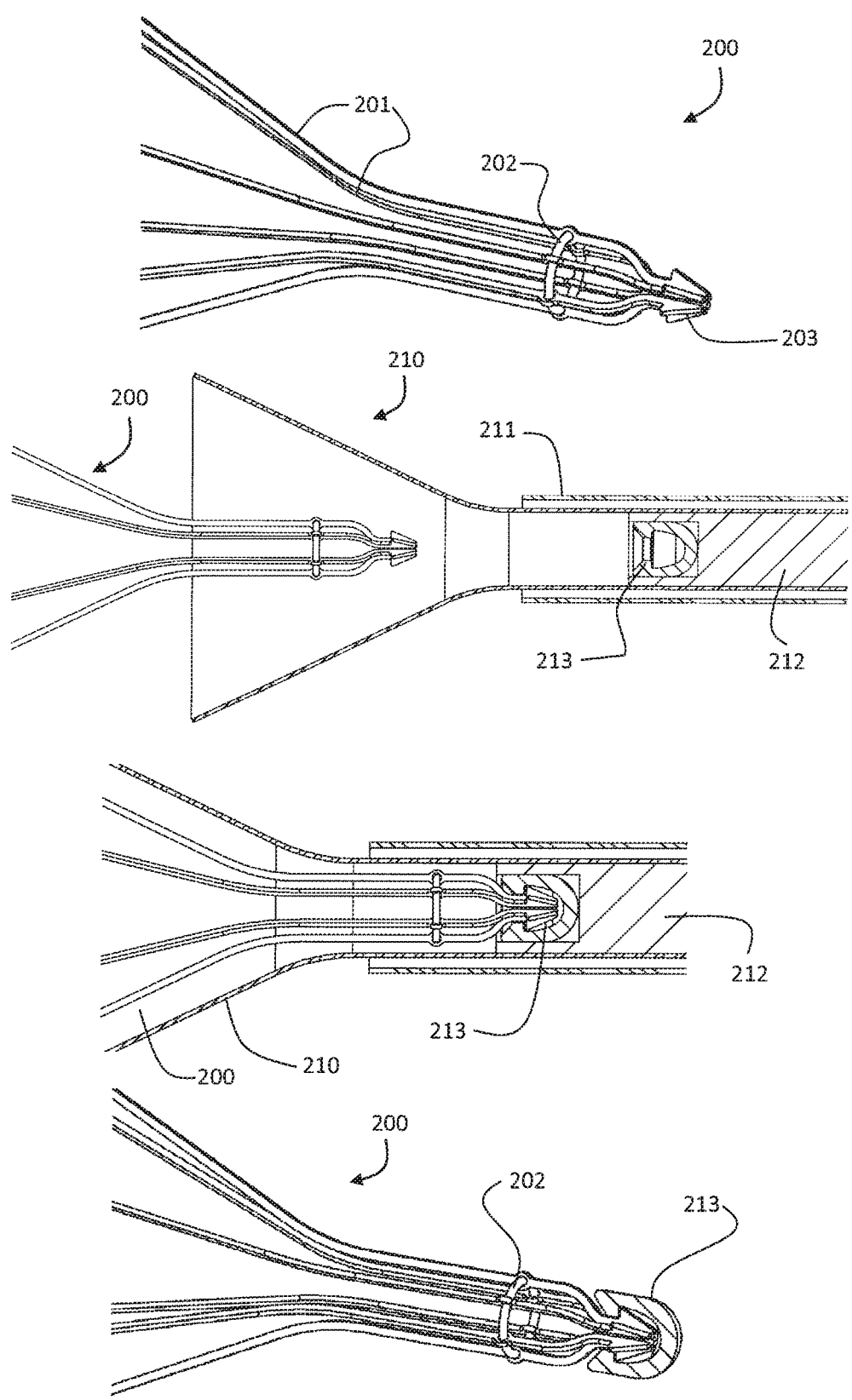
FIG. 65 is a set of views showing an alternative filter of the invention onto which a cup-shaped retainer is placed by a catheter.
Figure 66:
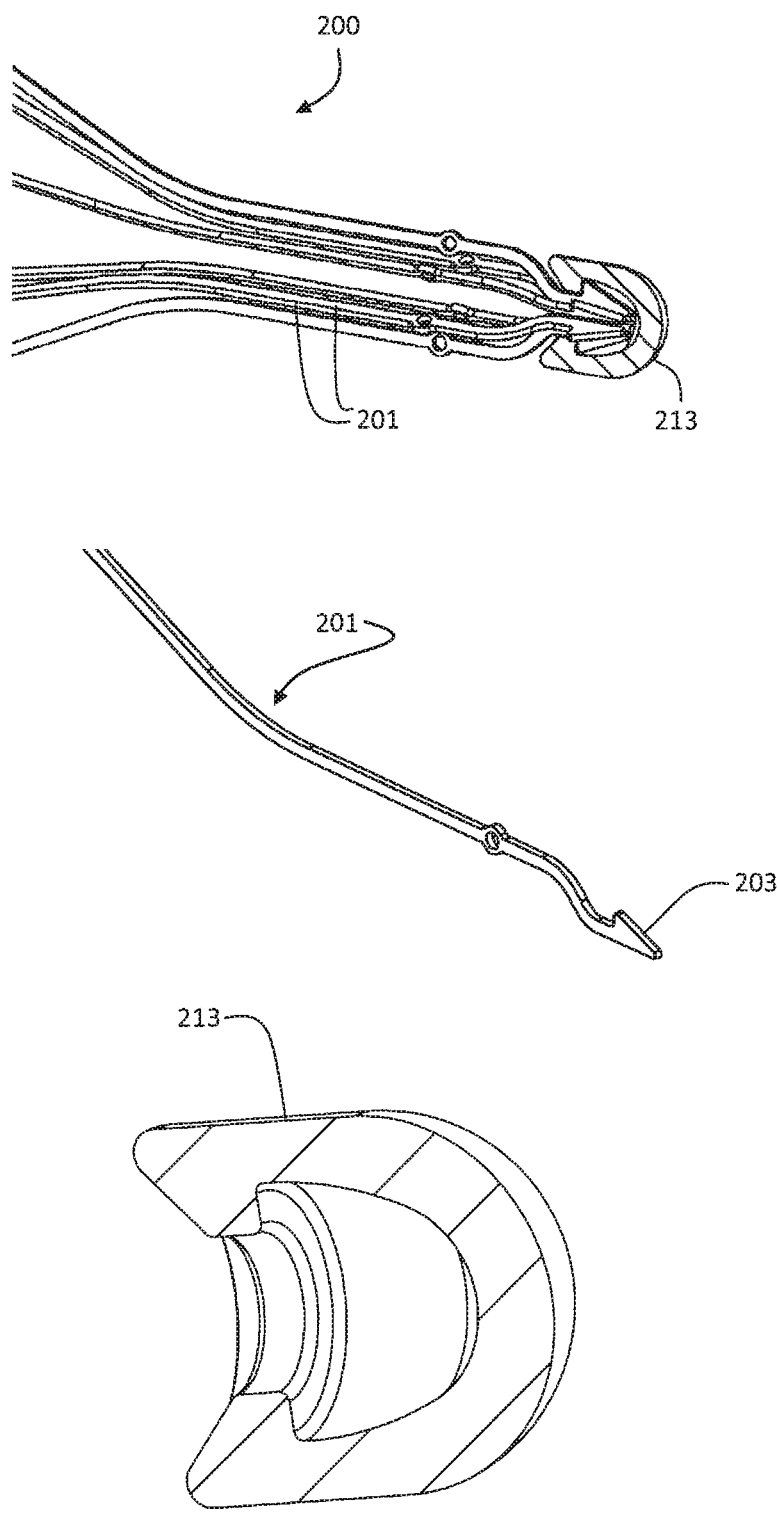
FIG. 66 is a set of views showing the filter elements and the retainer in more detail.

Referring to FIGS. 65 and 66 a filter 200 comprises filter elements 201 held by a biodegradable holder 202. The filter elements 201 terminate at the distal end with a tip 203 somewhat like an arrow head. For retaining the closed state beyond the predetermined period of time an expanded funnel 210 is moved by a catheter having a funnel sheath 211 and a central shaft 212. The catheter delivers a retainer 213 which is cup-shaped, with an internal rim. For delivery, after the delivery system is advanced to the site, the self-expanding locating funnel 210 is expanded by retracting the sheath 211. The funnel fits neatly over the, similarly shaped, filter. The assembly is advanced further and a slight force is applied for the retainer 213 to snap over the tips 203. This force is low to avoid damage to the vessel wall. The assembly is retracted and the sheath is advanced to collapse the funnel before removing it from the patient. An offset lumen may be provided in the catheter to allow passage of a guide wire and/or snare. The retainer 213 may have a hook on the distal end to allow removal at a later stage. The retainer may have a reception space on the distal end (like a miniature version of that on the proximal side) so that it could be releasably attached to a snap feature on the pusher, the locking force between the filter elements and the retainer would need to be greater than that between the retainer and the pusher in order to disengage from the pusher.

In another embodiment of the invention the retainer is selectively movable by application of an energy stimulus from a non-retaining configuration in which the filter 1 is not retained in the closed state, to a retaining configuration in which the filter 1 is retained in the closed state.

For example, the retainer may comprise a cure adhesive. The retainer may be selectively movable by application of ultraviolet light from the non-retaining configuration in which the filter 1 is not retained in the closed state, to the retaining configuration in which the filter 1 is retained in the closed state.

For example, the retainer may comprise a biostable polymer. The retainer may be selectively movable by application of heat or an electric current to cure the polymer from the non-retaining state in which the filter 1 is not retained in the closed state, to the retaining state in which the filter 1 is retained in the closed state.

For example the retainer may comprise a biostable polymer. The retainer may be selectively movable by application of heat or an electric current to transform a non restraining polymer arrangement in which the filter 1 is not retained in the closed state, into a restraining polymer arrangement through melt flow in which the filter 1 is retained in the closed state.

For example, the retainer may comprise a two-part epoxy system. The retainer may be selectively movable by addition of the second part from the non-retaining state in which the filter 1 is not retained in the closed state, to the retaining state in which the filter 1 is retained in the closed state.

For example, the retainer may be selectively movable by application of a magnetic field from the non-retaining configuration in which the filter 1 is not retained in the closed state, to the retaining configuration in which the filter 1 is retained in the closed state.

It is appreciated that the secondary retainers disclosed above can be manufactured using a biodegradable or a biostable material to extend the protection period temporarily or permanently. If a biodegradable secondary holder is selected, it is possible to perform an additional intervention to extend the protection period further.

It will be appreciated that more than one retainer may be employed to extend the period of time in which the filter 1 captures thrombus. For example in the case where a first retainer is biodegradable and/or bioabsorbable, a second retainer may be employed to further extend the period of time in which the filter 1 captures thrombus beyond biodegrading/bioabsorbing of the first retainer. Any of the retainers may be of any suitable form as described herein. The first retainer may be of the same type or of a different type of retainer as the second retainer.

The retaining members used to extend the protection period may also be used with multistage filters. Consider a double convertible cone filter with a coarse proximal filter and a fine distal filter that separates clot particles by size where smaller particles travel through the coarse proximal filter and are trapped by the fine distal filter. The fine distal filter is intended to capture smaller particles that would normally be clinically insignificant but would present a risk to a patient with poor pulmonary reserve. After the patient has recovered to the extent that pulmonary reserve is improved but pulmonary embolism is still a risk, it would be desirable to extend the protection period only for the coarse proximal filter. The coarse filter is less likely to become blocked with smaller clinically insignificant particles. Having the coarse filter proximal It is appreciated that the filter embodiments discussed above can be used for general embolic protection in any blood vessel.

It will also be appreciated that the invention is not limited to use with vena cava filters. The invention may also be employed to replace one or more bioresorbable materials in other vascular devices, such as a stent, with one or more biostable components.

The invention is not limited to the embodiments hereinbefore described, with reference to the accompanying drawings, which may be varied in construction and detail.

What is claimed is:

1. A vascular filter system comprising:
a vascular filter comprising at least one filter element, the filter being movable from a closed state adapted to capture thrombus passing through a blood vessel to an open state facilitating unrestricted blood flow, and
a holder adapted to hold the filter in the closed state for a predetermined period of time, said holder being biodegradable and/or bioabsorbable upon elapse of said predetermined period of time whereupon the filter is configured to move to the open state,
characterized in that the system further comprises a member adapted to at least temporarily extend a filtration period,
the member comprises a retainer adapted to at least temporarily retain the filter in the closed state beyond elapse of the predetermined period of time, and
the system comprises a delivery mechanism adapted to deliver the retainer to the filter when located in the blood vessel,
wherein the delivery mechanism is adapted to maintain a position of the filter relative to a blood vessel during delivery of the retainer, and to grasp the filter for delivery of the retainer,
wherein the retainer is extendable around at least part of the filter to retain the filter in the closed state, wherein at least part of the retainer is biodegradable and/or bioabsorbable.

2. A system as claimed in claim 1, wherein the retainer is adapted to clamp at least part of the filter to retain it in the closed state.

3. A system as claimed in claim 1, wherein the retainer is adapted to tie at least part of the filter to retain it in a capturing state.

4. A system as claimed in claim 1, wherein the retainer is configured to be located in a region of a centre of the filter.

5. A system as claimed in claim 1, wherein the retainer is configured to be located in a region of the side of the filter.

6. A system as claimed in claim 1, wherein the retainer is movable between a delivery state and a retaining state, and wherein the retainer is biased towards the retaining state.

7. A system as claimed in claim 1, wherein the retainer is configured to releasably retain the filter in the closed state.

8. A system as claimed in claim 1, wherein the retainer is changeable, when engaging the filter, from a non-retaining state in which the filter is not retained to a retaining state in which the filter is retained.

9. A system as claimed in claim 8, wherein the retainer is changeable from the non-retaining state to the retaining state responsive to an external intervention.

10. A system as claimed in claim 8, wherein the retainer is changeable by rotation on threads to move with respect to the filter.

11. A system as claimed in claim 1, wherein at least part of the retainer is extendable through an opening between adjacent filter elements to retain the filter elements in the closed state beyond elapse of the predetermined period of time.

12. A system as claimed in claim 1, wherein at least part of the retainer is extendable through an opening in a filter element to retain the filter elements in the closed state beyond elapse of the predetermined period of time.

\* \* \* \* \*